United States Patent
Remes

(10) Patent No.: US 11,769,655 B2
(45) Date of Patent: Sep. 26, 2023

(54) SYSTEMS AND METHODS FOR PERFORMING MULTIPLEXED TARGETED MASS SPECTROMETRY

(71) Applicant: Thermo Finnigan LLC, San Jose, CA (US)

(72) Inventor: Philip M. Remes, Livermore, CA (US)

(73) Assignee: Thermo Finnigan LLC, San Jose, CA (US)

( * ) Notice: Subject to any disclaimer, the term of this patent is extended or adjusted under 35 U.S.C. 154(b) by 74 days.

(21) Appl. No.: 17/494,484

(22) Filed: Oct. 5, 2021

(65) Prior Publication Data

US 2023/0108254 A1    Apr. 6, 2023

(51) Int. Cl.
*H01J 49/00* (2006.01)
*G01N 30/72* (2006.01)
*H01J 49/04* (2006.01)

(52) U.S. Cl.
CPC ...... *H01J 49/0036* (2013.01); *G01N 30/7233* (2013.01); *H01J 49/0031* (2013.01); *H01J 49/0431* (2013.01)

(58) Field of Classification Search
CPC .............. H01J 49/0036; H01J 49/0031; H01J 49/0431; G01N 30/7233
USPC ........................................ 250/281, 282, 288
See application file for complete search history.

(56) References Cited

U.S. PATENT DOCUMENTS

| | | | | |
|---|---|---|---|---|
| 9,048,074 B2* | 6/2015 | Senko | .................. | H01J 49/0031 |
| 10,665,440 B1* | 5/2020 | Remes | ................. | H01J 49/0036 |
| 2014/0339421 A1* | 11/2014 | Senko | ................. | H01J 49/0031 |
| | | | | 250/281 |

OTHER PUBLICATIONS

Tian, et al ("Chemical Isotope Labeling for Quantitative Proteomics," Mass Spectrometry Reviews, Jun. 6, 2021, pp. 1-31) (Year: 2021).*
Pappireddi, et al ("A Review on Quantitative Multiplexed Proteomics," Chemobiochem, 20(10) 2019, pp. 1210-1224, XP055678910 (Year: 2019).*
Barshop, et al ("Sequential Windowed Acquisition of Reporter Masses or Quantitation-First Proteomics," Journal of Proteome Research, 18(4), 2019, pp. 1893-1901 (Year: 2019).*
Tian X et al: "Chemical isotope labeling for quantitative proteomics", Mass Spectrometry Reviews, Jun. 6, 2021, 1-31, XP055951707.
Pappireddi N et al: "A Review on Quantitative Multiplexed Proteomics", Chembiochem, 20(10), 2019, 1210-1224, XP055678910.

(Continued)

*Primary Examiner* — Michael Maskell

(57) ABSTRACT

A method of performing targeted multiplexed mass spectrometry includes performing, at a mass spectrometer, a targeted MS3 analysis of an isobaric tag-labeled target analyte included in a multiplex sample eluting from a column. The targeted MS3 analysis is performed during an acquisition segment scheduled based on an expected retention time of the isobaric tag-labeled target analyte. The method further includes performing, during the acquisition segment, a plurality of MS2 analyses of product ions derived from components included in the multiplex sample and eluting from the column. The method further includes determining, based on MS3 mass spectra acquired by the targeted MS3 analysis and MS2 mass spectra acquired by the plurality of MS2 analyses, a relative quantity of the isobaric tag-labeled target analyte in the multiplex sample.

40 Claims, 11 Drawing Sheets

(56) References Cited

OTHER PUBLICATIONS

Barshop W D et al: "Sequential Windowed Acquisition of Reporter Masses or Quantitation-First Proteomics", Journal of Proteome Research, 18(4), 2019, 1893-1901, XP093012400.
International Search Report and Written Opinion dated Jan. 19, 2023, to PCT Application No. PCT/IB2022/059515.

* cited by examiner

SYSTEMS AND METHODS FOR PERFORMING MULTIPLEXED TARGETED MASS SPECTROMETRY

BACKGROUND INFORMATION

A mass spectrometer is a sensitive instrument that may be used to detect, identify, and/or quantify molecules based on their mass-to-charge ratio (m/z). A mass spectrometer generally includes an ion source for generating ions from components included in the sample, a mass analyzer for separating the ions based on their m/z, and an ion detector for detecting the separated ions. The mass spectrometer may be connected to a computer-based software platform that uses data from the ion detector to construct a mass spectrum that shows a relative abundance of each of the detected ions as a function of m/z. The m/z of ions may be used to detect and quantify molecules in simple and complex mixtures. A separation device such as a liquid chromatograph (LC) or gas chromatograph (GC) may be coupled to the mass spectrometer (MS) in a combined system (e.g., an LC-MS or GC-MS system) to separate components included in the sample before the components are introduced to the mass spectrometer.

The selective detection and quantitation of a specific target analyte of interest in a complex mixture is often very difficult, even with targeted acquisition. For example, in proteomics research, a peptide target of interest may be included in a complex biological matrix composed of a mixture of tens of thousands of peptides with abundances spanning many orders of magnitude. Tandem mass spectrometry (MS/MS or MS2) may be used for the quantitation of a target molecule in a complex mixture. For example, in a refined targeted acquisition technique known as internal standard triggered-parallel reaction monitoring (IS-PRM), a sample containing a peptide target may be spiked with a known amount of the corresponding internal standard (IS) (e.g., a synthetic peptide with the same amino acid sequence but containing heavy stable isotope(s)) and scanned by the instrument in a dual-mode combining single stage and tandem mass spectrometry. Detection of the internal standard triggers the mass spectrometer to monitor for the specific peptide target of interest.

Multiplexing with the use of isobaric tags, such as tandem mass tag (TMT) reagents or isobaric tags for relative and absolute quantitation (iTRAQ®) (AB Sciex Pte. Ltd.) reagents, may increase sample throughput. In brief, isobaric tags are compounds that react with and attach to peptides. Isobaric tags have two regions: a reporter region and a balance region. Versions of isobaric tags have been created that all have the same exact total mass of reporter region plus balance region, but the reporter region mass and the balance region mass for each version is different. Multiple individual samples may be multiplexed by labeling analytes (e.g., peptides) in each sample with a different version of the isobaric tag, mixing all the samples together, and analyzing the combined samples via LC-MS or GC-MS in one experiment. The same isobaric tag-labeled peptides across the various individual samples all have the same m/z, but when they are fragmented by MS2 the reporter region of the isobaric tag falls off and reporter ions of different m/z may be analyzed by MS2. The relative intensity of the reporter ions at their various m/z are indicative of the relative concentrations of the analytes in each individual sample.

However, every isobaric tag-labeled analyte in a particular individual sample fragments to form the same reporter ions. Thus, when quantitating a particular target analyte in a sample, reporter ions from other non-target (contaminating or background) analytes that co-elute and are co-isolated with the target analyte may also be detected, leading to so-called "ratio distortion" and inaccurate quantitation of the target analyte. These problems have been addressed by performing targeted MS/MS/MS (MS3) analyses that use data dependent acquisition (DDA) to analyze the isobaric tag-labeled target analytes.

For example, periodic MS survey scans may be performed, and any precursor ions that meet certain criteria are flagged and trigger MS2 analyses on those ions. If the MS2 mass spectra indicate the presence of product ions that are likely to have isobaric tags, the product ions are isolated and fragmented, releasing the reporter ions as second generation product ions. The m/z region of the reporter ions is then measured using a targeted MS3 analysis. This double-filtering process removes contaminant and background analytes prior to detection of the reporter ions. Thus, a targeted MS3 analysis may be performed by using an MS2 DDA analysis.

A conventional implementation of a multiplex targeted TMT MS3 concept includes the "triggered by offset, multiplexed, accurate-mass, high-resolution, and absolute quantification" (TOMAHAQ) method. This method uses spiked-in internal standard peptides at high concentration to be detected in the MS survey scan, an MS2 DDA confirming scan, and a quantifying targeted MS3 scan. Although useful in certain cases, the reliance on internal standards makes it prohibitively expensive and complex for some researchers, and the method may not be sufficiently effective on linear ion trap mass analyzers.

Another conventional implementation of the multiplex targeted TMT MS3 concept is Barshop's Sequential Windows Acquisition of Reporter Masses for Quantitation-First. In this approach, a sample is first characterized by low-accuracy MS2 data-independent acquisition (DIA) analyses to find regions of time and m/z that contain reporter ions with nominally large fold changes. A targeted MS2 analysis is then performed that scans for certain m/z windows and times, and then a data-dependent multiplexed MS3 analysis is performed for any MS2 mass spectra with fragments that meet certain criteria. This method does not rely on internal standards like TOMAHAQ, but its reliance on MS2 reporter ion measurements to make decisions about what to target in MS3 could be misguided or too narrowing. Moreover, the use of data dependence may still lead to the "missing values" problem in which certain analytes cannot be identified or quantified in certain samples due to the stochastic nature of DDA.

For at least these reasons, there is a need for improved methods and systems for performing multiplexed targeted mass spectrometry.

SUMMARY

The following description presents a simplified summary of one or more aspects of the methods and systems described herein in order to provide a basic understanding of such aspects. This summary is not an extensive overview of all contemplated aspects and is intended to neither identify key or critical elements of all aspects nor delineate the scope of any or all aspects. Its sole purpose is to present some concepts of one or more aspects of the methods and systems described herein in a simplified form as a prelude to the more detailed description that is presented below.

In some illustrative embodiments, a method of performing targeted mass spectrometry, comprises: performing, at a mass spectrometer, a targeted MS3 analysis of an isobaric tag-labeled target analyte included in a multiplex sample eluting from a column, wherein the targeted MS3 analysis is performed during an acquisition segment scheduled based on an expected retention time of the isobaric tag-labeled target analyte; performing, during the acquisition segment, a plurality of MS2 analyses of product ions derived from components included in the multiplex sample and eluting from the column; and determining, based on MS3 mass spectra acquired by the targeted MS3 analysis and MS2 mass spectra acquired by the plurality of MS2 analyses, a relative quantity of the isobaric tag-labeled target analyte in the multiplex sample.

In some illustrative embodiments, the determining the relative quantity of the isobaric tag-labeled target analyte comprises identifying, based on the MS2 mass spectra, MS3 mass peaks included in the MS3 mass spectra and representative of the isobaric tag-labeled target analyte.

In some illustrative embodiments, the identifying the MS3 mass peaks representative of the isobaric tag-labeled target analyte comprises spectral matching of the MS2 mass spectra with library MS2 mass spectra for the isobaric tag-labeled target analyte.

In some illustrative embodiments, the identifying the MS3 mass peaks representative of the isobaric tag-labeled target analyte comprises: determining, based at least in part on the MS2 mass spectra, a quality score of mass peaks included in the MS3 mass spectra; and identifying the MS3 mass peaks representative of the isobaric tag-labeled target analyte based on the quality score of the MS3 mass peaks included in the MS3 mass spectra.

In some illustrative embodiments, an isolation width of the MS2 analyses is between about 10 m/z and about 20 m/z.

In some illustrative embodiments, a spectral range of the MS2 analyses ranges from about 200 m/z to about 1600 m/z.

In some illustrative embodiments, a precursor range of the MS2 analyses ranges from about 400 m/z to about 1000 m/z.

In some illustrative embodiments, each MS2 analysis is targeted for ions produced from target analytes expected to elute from the column during the MS2 analysis.

In some illustrative embodiments, the MS2 analyses are performed with a frequency between about once every second and about once every three seconds.

In some illustrative embodiments, the MS2 analyses are scheduled based on the scheduled acquisition segment.

In some illustrative embodiments, the mass spectrometer comprises a linear ion trap mass analyzer.

In some illustrative embodiments, a method of performing multiplexed targeted mass spectrometry comprises: acquiring, at a mass spectrometer by a plurality of targeted MS3 analyses during a plurality of acquisition segments, MS3 mass spectra of reporter ions dissociated from a plurality of isobaric tag-labeled target analytes included in a multiplex sample eluting from a column, wherein: the multiplex sample comprises a combination of a plurality of individual samples each including one or more of the isobaric tag-labeled target analytes, the one or more target analytes included in each individual sample are labeled with a distinct version of an isobaric tag comprising a reporter region from which the reporter ions are derived, and each targeted MS3 analysis is performed during an acquisition segment scheduled based on an expected retention time of a target analyte included in the plurality of target analytes; and periodically acquiring, at the mass spectrometer by a plurality of MS2 analyses performed during the plurality of acquisition segments, MS2 mass spectra of product ions derived from the plurality of target analytes.

In some illustrative embodiments, each targeted MS3 analysis comprises acquisition of a plurality of MS3 mass spectra.

In some illustrative embodiments, the method further comprises determining a relative quantity of a target analyte included in the plurality of target analytes across the plurality of individual samples based on MS2 mass spectra acquired during an acquisition segment for the target analyte and MS3 mass spectra acquired during the acquisition segment for the target analyte.

In some illustrative embodiments, the determining the relative quantity of the target analyte comprises identifying, based on the MS2 mass spectra acquired during the acquisition segment for the target analyte, MS3 mass peaks representative of the target analyte, the MS3 mass peaks representative of the target analyte comprising mass peaks in the MS3 mass spectra acquired during the acquisition segment for the target analyte.

In some illustrative embodiments, the identifying the MS3 mass peaks representative of the target analyte is based on spectral matching of the MS2 mass spectra acquired during the acquisition segment for the target analyte with library MS2 mass spectra for the target analyte.

In some illustrative embodiments, the method further comprises: determining a quality score for each MS3 mass peak acquired during the acquisition segment for the target analyte; wherein the identifying the MS3 mass peaks representative of the target analyte is based on the quality score for each MS3 mass peak acquired during the acquisition segment for the target analyte.

In some illustrative embodiments, the quality score is based on one or more of an MS2 spectral similarity score for each MS2 mass peak, an MS2 mass peak area, and an MS3 mass peak area.

In some illustrative embodiments, the MS2 analyses are scheduled based on the scheduled acquisition segments.

In some illustrative embodiments, the method further comprises adjusting an acquisition segment of a target analyte based on the MS2 mass spectra.

In some illustrative embodiments, the method further comprises: supplying a multiplex sample to the column; directing the plurality of target analytes included in the multiplex sample and eluting from the column to the mass spectrometer; and producing ions from the plurality of target analytes; wherein the product ions and the reporter ions are derived from the ions produced from the plurality of target analytes.

In some illustrative embodiments, a system for performing multiplexed targeted mass spectrometry comprises: a chromatography column configured to receive a multiplex sample and separate components included in the multiplex sample, wherein: the components included in the multiplex sample include a plurality of target analytes; the multiplex sample comprises a combination of a plurality of individual samples each including one or more of the target analytes; and the one or more target analytes included in each individual sample are labeled with a distinct version of an isobaric tag comprising a reporter region; a mass spectrometer configured to receive the components eluting from the chromatography column and mass analyze ions produced from the components; and a computing device configured to: acquire, by a plurality of targeted MS3 analyses during a plurality of acquisition segments, MS3 mass spectra of reporter ions dissociated from the plurality of target analytes included in the multiplex sample, wherein: each reporter ion is derived from the reporter region of an isobaric tag; and each targeted MS3 analysis is performed during an acquisition segment scheduled based on an expected retention time of a target analyte included in the plurality of target analytes; and periodically acquire, by a plurality of MS2 analyses performed during the plurality of acquisition segments, MS2 mass spectra of product ions derived from the plurality of target analytes.

In some illustrative embodiments, the computing device is further configured to: determine a relative quantity of a target analyte included in the plurality of target analytes across the plurality of individual samples based on MS2 mass spectra acquired during an acquisition segment for the target analyte and MS3 mass spectra acquired during the acquisition segment for the target analyte.

In some illustrative embodiments, the determining the relative quantity of the target analyte comprises identifying, based on the MS2 mass spectra acquired during the acquisition segment for the target analyte, MS3 mass peaks representative of the target analyte, the MS3 mass peaks representative of the target analyte comprising mass peaks in the MS3 mass spectra acquired during the acquisition segment for the target analyte.

In some illustrative embodiments, the computing device is further configured to: determine a quality score for each MS3 mass peak acquired during the acquisition segment for the target analyte; wherein the identifying the MS3 mass peaks representative of the target analyte is based on the quality score for each MS3 mass peak acquired during the acquisition segment for the target analyte.

In some illustrative embodiments, the quality score is based on one or more of an MS2 spectral similarity score for each MS2 mass peak, an MS2 mass peak area, and an MS3 mass peak area.

In some illustrative embodiments, the computing device is further configured to: adjust an acquisition segment of a target analyte based on the MS2 mass spectra.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
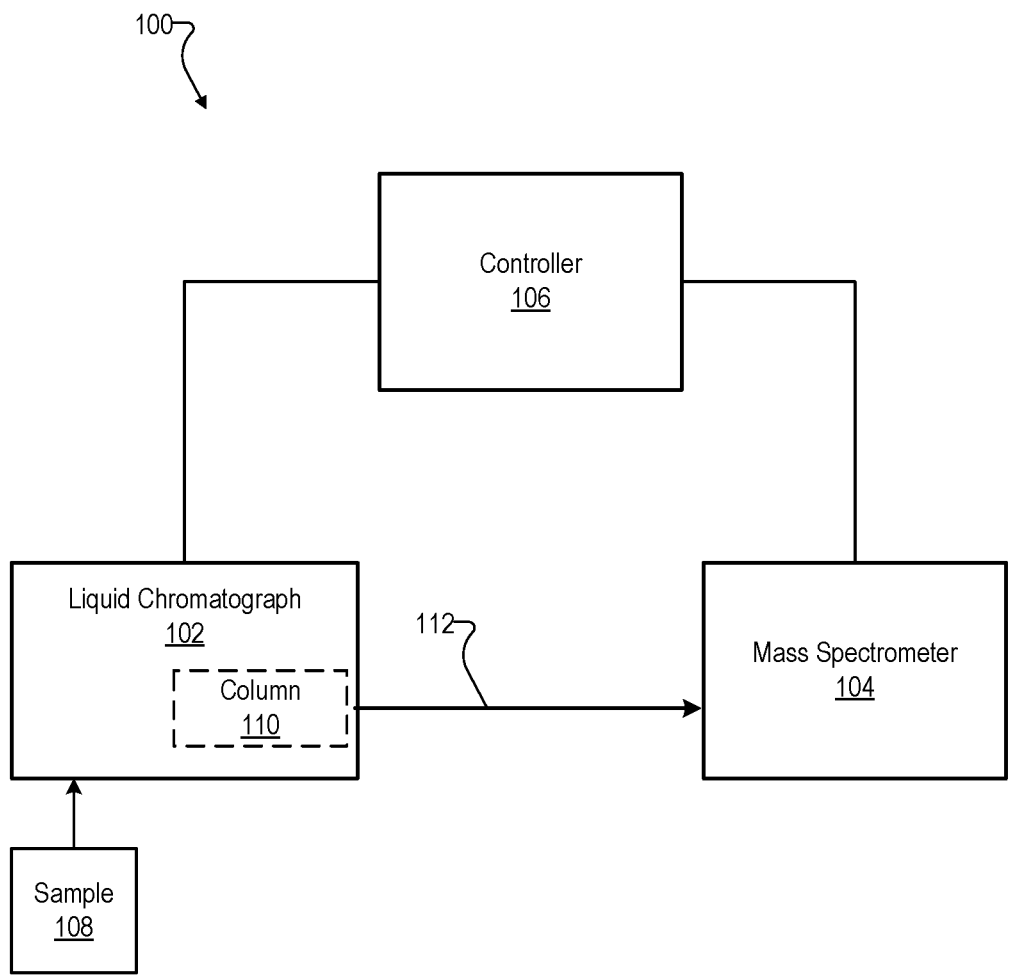
FIG. 1 shows an illustrative LC-MS/MS/MS system including a liquid chromatograph and a mass spectrometer.

Methods and systems for performing multiplexed targeted mass spectrometry are described herein. An improved method of multiplexed targeted mass spectrometry includes performing, during retention time-scheduled acquisition segments, targeted MS3 analyses of target analytes included in an eluting multiplex sample and performing periodic MS2 analyses during the acquisition segments of the targeted MS3 analyses. Based on MS3 mass spectra acquired by the targeted MS3 analysis and MS2 mass spectra acquired by the plurality of MS2 analyses, a relative quantity of the isobaric tag-labeled target analyte in the multiplex sample may be determined. For example, the targeted MS3 analyses provide reporter ion quantitation with low ratio distortion for relative quantitation of the target analytes, and the periodic MS2 analyses provide confirmation of the target analyte identity for quantitation of the target analyte. The periodic MS2 analyses may also be used for retention time alignment, which allows the retention time-scheduled MS3 acquisition segments to be narrower than otherwise possible, thereby increasing throughput and/or sensitivity. These and other illustrative methods and systems for multiplexed targeted mass spectrometry will be described in more detail below.

The multiplexed targeted mass spectrometry experiments described herein do not rely on data dependent acquisitions (DDAs) or the use of expensive internal standards, thus enabling low cost, reproducible targeted MS3 analyses for relative quantitation of target analytes with low ratio distortion and without missing values across experiments. Despite the loss of overall experimental coverage (number of peptides quantified), the systems and methods described herein are amenable to lower-cost mass analyzers, such as linear ion traps, and provide high throughput with targeted multiplexed MS3 analysis of hundreds to thousands of target analytes. Accordingly, the methods and systems described herein may be suitable for large cohort studies, especially those using multi-channel (e.g., 9 or more) isobaric tags.

The multiplexed targeted mass spectrometry methods described herein have better throughput than traditional targeted MS2 and MS3 methods by using isobaric tag multiplexing on the sample dimension. Additionally, the methods described herein may not need to use a high MSn sampling rate because the methods quantitate based only on the ratios of reporter ion fragments, thereby obviating the need to fully resolve the LC peaks as in traditional targeted MS2 and MS3.

Various embodiments will now be described in more detail with reference to the figures. The systems and methods described herein may provide one or more of the benefits mentioned above and/or various additional and/or alternative benefits that will be made apparent herein.

In some implementations, the methods and systems for performing ion population regulation may be used in conjunction with a combined separation-mass spectrometry system, such as an LC-MS/MS/MS system. As such, an LC-MS/MS/MS system will now be described. The described LC-MS/MS/MS system is illustrative and not limiting. The methods and systems described herein may operate as part of or in conjunction with the LC-MS/MS/MS system described herein and/or with any other suitable separation-mass spectrometry system, including a high-performance liquid chromatography-mass spectrometry (HPLC-MS/MS/MS) system, a gas chromatography-mass spectrometry (GC-MS/MS/MS) system, or a capillary electrophoresis-mass spectrometry (CE-MS/MS/MS) system. The methods and systems described herein may also operate in conjunction with any other continuous flow sample source, such as a flow-injection MS system (FI-MS/MS/MS) in which analytes are injected into a mobile phase (without separation in a column) and enter the mass spectrometer with time-dependent variations in intensity (e.g., Gaussian-like peaks).

FIG. 1 shows an illustrative LC-MS/MS/MS system 100. LC-MS/MS/MS system 100 includes a liquid chromatograph 102, a mass spectrometer 104, and a controller 106. Liquid chromatograph 102 is configured to separate, over time, components (e.g., analytes) within a sample 108 that is injected into liquid chromatograph 102. Sample 108 may include, for example, chemical components (e.g., molecules, ions, etc.) and/or biological components (e.g., metabolites, proteins, peptides, lipids, etc.) for detection and analysis by LC-MS/MS/MS system 100. Liquid chromatograph 102 may be implemented by any liquid chromatograph as may suit a particular implementation. In liquid chromatograph 102, sample 108 may be injected into a mobile phase (e.g., a solvent), which carries sample 108 through a column 110 containing a stationary phase (e.g., an adsorbent packing material). As the mobile phase passes through column 110, components within sample 108 elute from column 110 at different times based on, for example, their size, their affinity to the stationary phase, their polarity, and/or their hydrophobicity.

A detector (e.g., an ion detector component of mass spectrometer 104, an ion-electron converter and electron multiplier, etc.) may measure the relative intensity of a signal modulated by each separated component in eluate 112 from column 110. Data generated by the detector may be represented as a chromatogram, which plots retention time on the x-axis and a signal representative of the relative intensity on the y-axis. The retention time of a component is generally measured as the period of time between injection of sample 108 into the mobile phase and the relative intensity peak maximum after chromatographic separation. In some examples, the relative intensity may be correlated to or representative of relative abundance of the separated components. Data generated by liquid chromatograph 102 may be output to controller 106.

In some cases, particularly in analyses of complex mixtures, multiple different components (e.g., isobarically labeled peptides) in sample 108 may co-elute from column 110 at approximately the same time, and thus may have the same or similar retention times. As a result, determination of the relative intensity of the individual components within sample 108 requires further separation of signals attributable to the individual components. To this end, liquid chromatograph 102 directs components included in eluate 112 to mass spectrometer 104 for identification and/or quantification of one or more of the components.

Mass spectrometer 104 is configured to produce ions from the components received from liquid chromatograph 102 and sort or separate the produced ions based on m/z of the ions. A detector in mass spectrometer 104 measures the intensity of the signal produced by the ions. As used herein, "intensity" or "signal intensity" may refer to any suitable metric, such as abundance, relative abundance, ion count, intensity, or relative intensity. Data generated by the detector may be represented by mass spectra, which plot the intensity of the observed signal as a function of m/z of the detected ions. Data acquired by mass spectrometer 104 may be output to controller 106. Mass spectrometer 104 may be implemented by a suitable multi-stage mass spectrometer having three or more mass analysis stages. An illustrative mass spectrometer 104 will be described below in more detail.

Controller 106 may be communicatively coupled with, and configured to control operations of, LC-MS/MS/MS system 100. Controller 106 may include any suitable hardware (e.g., a processor, circuitry, memory, etc.) and/or software configured to control operations of and/or interface with the various components of LC-MS/MS/MS system 100. For example, controller 106 may be configured to acquire data acquired over time by liquid chromatograph 102 and mass spectrometer 104. The data may include a series of mass spectra including intensity values of ions produced from the components of sample 108 as a function of m/z of the ions. The data may be represented in a three-dimensional map in which time (e.g., retention time) is plotted along an x-axis, m/z is plotted along a y-axis, and intensity is plotted along a z-axis. Spectral features on the map (e.g., peaks of intensity) represent detection by LC-MS/MS/MS system 100 of ions produced from various components included in sample 108. The x-axis and z-axis of the map may be used to generate a mass chromatogram that plots intensity as a function of time for a selected m/z (e.g., an extracted ion chromatogram (XIC)) or for a full m/z spectrum (e.g., a total ion current (TIC)). As used herein, a "selected m/z" may include a specific m/z with or without a mass tolerance window or a narrow range of m/z. The y-axis and z-axis of the map may be used to generate mass spectra, each mass spectrum plotting intensity as a function of m/z for a particular acquisition (e.g., for each MS scan or MS/MS scan).

Figure 2:
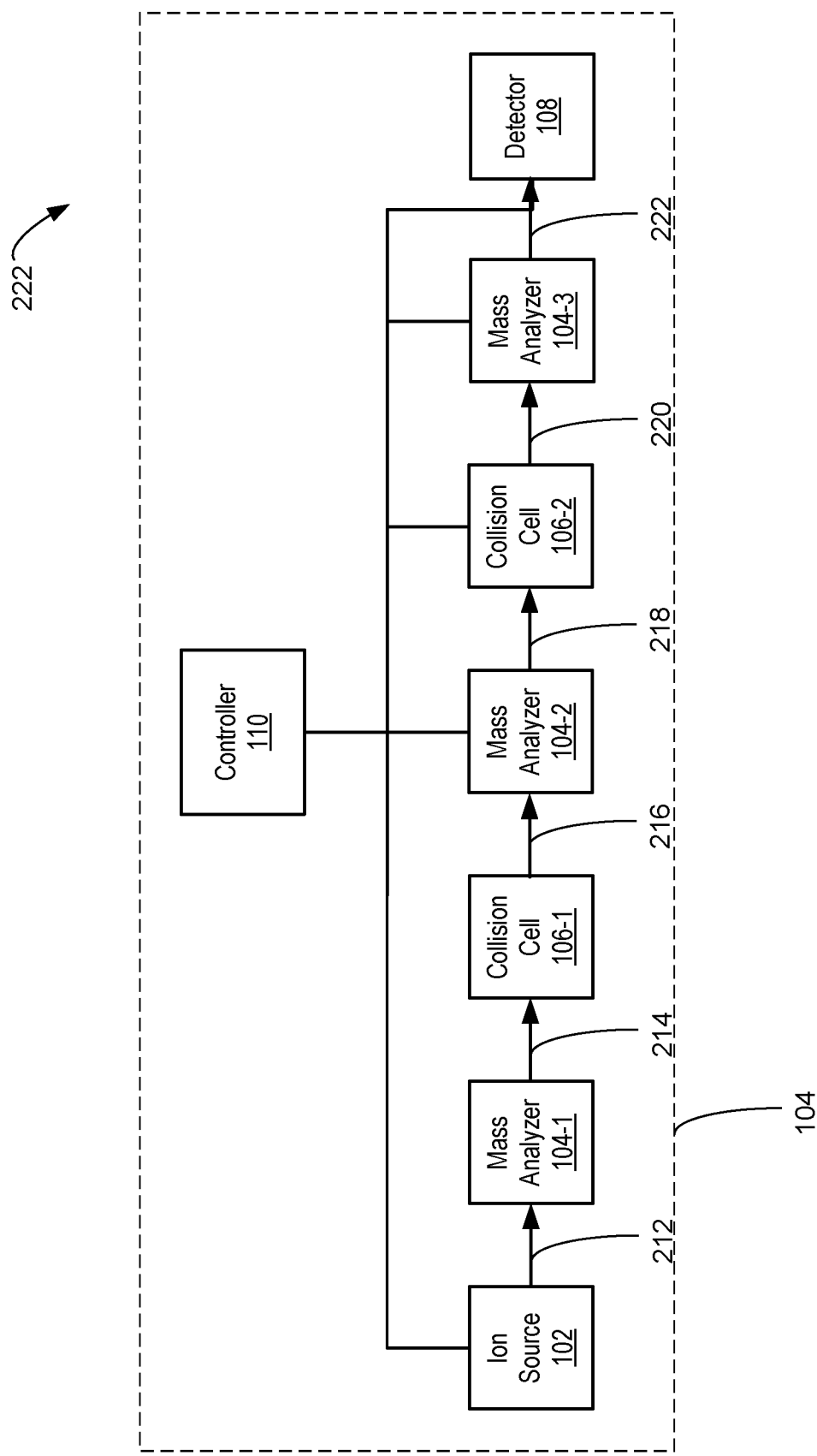
FIG. 2 shows an illustrative implementation of the mass spectrometer of FIG. 1 including an ion accumulator.

FIG. 2 shows a functional diagram of an illustrative implementation 200 of mass spectrometer 104. As shown, mass spectrometer 104 is a three-stage mass spectrometer configured to perform three-stage mass spectrometry (denoted MS/MS/MS or MS3). While FIG. 2 shows that mass spectrometer 104 is multi-stage in space, mass spectrometer 104 may alternatively be multi-stage in time. Mass spectrometer 104 includes an ion source 202, first to third mass analyzers 204-1, 204-2, and 204-3, first and second collision cells 206-1 and 206-2, a detector 208, and a controller 210. Mass spectrometer 104 may further include any additional or alternative components not shown as may suit a particular implementation (e.g., ion optics, filters, ion storage devices, ion mobility analyzers, etc.).

Ion source 202 is configured to produce ions 212 from the components eluting from liquid chromatograph 102 and deliver ions 212 to first mass analyzer 204-1. Ion source 202 may use any suitable ionization technique, including without limitation electron ionization, chemical ionization, matrix assisted laser desorption/ionization, electrospray ionization, atmospheric pressure chemical ionization, atmospheric pressure photoionization, inductively coupled plasma, and the like. Ion source 202 may include various components for producing ions 212 from components included in sample 108 and delivering ions 212 to first mass analyzer 204-1.

First mass analyzer 204-1 is configured to separate or filter ions 212 according to m/z and/or perform a mass analysis of ions 212 and provide first precursor ions 214 to first collision cell 206-1. First collision cell 206-1 is configured to receive and fragment first precursor ions 214 to produce first generation product ions 216. First generation product ions 216 are provided to second mass analyzer 204-2, which is configured to separate or filter first generation product ions 216 according to m/z and/or perform a mass analysis of first generation product ions 216 (e.g., by MS2) and provide second precursor ions 218 to second collision cell 206-2. Second collision cell 206-2 is configured to receive and fragment second precursor ions 218 to produce second generation product ions 220. Second generation product ions 220 are provided to third mass analyzer 204-3. Third mass analyzer 204-3 is configured to separate or filter second generation product ions 220 according to m/z and/or perform a mass analysis of ions 220 (e.g., by MS3) and provide ions 222 to detector 208.

Mass analyzers 204 may be the same or different and may be implemented by any suitable mass analyzer, such as a quadrupole mass filter, an ion trap (e.g., a linear quadrupole ion trap, a three-dimensional quadrupole ion trap, a cylindrical ion trap, a toroidal ion trap, etc.), a time-of-flight (TOF) mass analyzer, an electrostatic trap mass analyzer (e.g. an orbital electrostatic trap such as an Orbitrap mass analyzer, a Kingdon trap, etc.), a Fourier transform ion cyclotron resonance (FT-ICR) mass analyzer, a sector mass analyzer, and the like.

Collision cells 206 may be the same or different and may be implemented by any suitable device configured to produce product ions by fragmentation or dissociation of precursor ions. The term "collision cell," as used herein, may include any structure arranged to produce product ions via controlled dissociation processes or ion-ion reaction processes and is not limited to devices employed for collisionally-activated dissociation. A collision cell 206 may be configured to fragment ions using collision induced dissociation (CID), electron transfer dissociation (ETD), electron capture dissociation (ECD), photo induced dissociation (PID), surface induced dissociation (SID), and the like.

Ion detector 208 is configured to detect ions at each of a variety of different m/z and responsively generate an electrical signal representative of ion intensity. The electrical signal is transmitted to controller 210 for processing, such as to construct a mass spectrum of the detected ions. For example, third mass analyzer 204-3 may emit an emission beam of ions 222 to detector 208, which is configured to detect ions 222 and generate or provide data that can be used by controller 210 (or another computing device) to construct a mass spectrum. Ion detector 208 may be implemented by any suitable detection device, including without limitation an electron multiplier, a Faraday cup, and the like.

Controller 210 may be communicatively coupled with, and configured to control various operations of, mass spectrometer 104. For example, controller 210 may be configured to control operation of various hardware components included in ion source 202, mass analyzers 204, collision cells 206, and/or detector 208. To illustrate, controller 210 may be configured to control an accumulation time of mass analyzers 204, control an oscillatory voltage power supply and/or a DC power supply to supply an RF voltage and/or a DC voltage to mass analyzers 204, adjust values of the RF voltage and DC voltage to select an effective m/z (including a mass tolerance window) for analysis, and adjust the sensitivity of ion detector 208 (e.g., by adjusting the detector gain).

Controller 210 may also include and/or provide a user interface configured to enable interaction between a user of mass spectrometer 104 and controller 210. The user may interact with controller 210 via the user interface by tactile, visual, auditory, and/or other sensory type communication. For example, the user interface may include a display device (e.g., liquid crystal display (LCD) display screen, a touch screen, etc.) for displaying information (e.g., mass spectra, notifications, etc.) to the user. The user interface may also include an input device (e.g., a keyboard, a mouse, a touchscreen device, etc.) that allows the user to provide input to controller 210. In other examples the display device and/or input device may be separate from, but communicatively coupled to, controller 210. For instance, the display device and the input device may be included in a computer (e.g., a desktop computer, a laptop computer, a mobile device, etc.) communicatively connected to controller 210 by way of a wired connection (e.g., by one or more cables) and/or a wireless connection (e.g., Wi-Fi, Bluetooth, near-field communication, etc.).

Controller 210 may include any suitable hardware (e.g., a processor, circuitry, memory, etc.) and/or software as may serve a particular implementation. While FIG. 2 shows that controller 210 is included in mass spectrometer 104, controller 210 may alternatively be implemented in whole or in part separately from mass spectrometer 104, such as by a computing device communicatively coupled to mass spectrometer 104 by way of a wired connection (e.g., a cable) and/or a network (e.g., a local area network, a wireless network (e.g., Wi-Fi), a wide area network, the Internet, a cellular data network, etc.). In some examples, controller 210 may be implemented in whole or in part by controller 106 (and vice versa).

Figure 3:
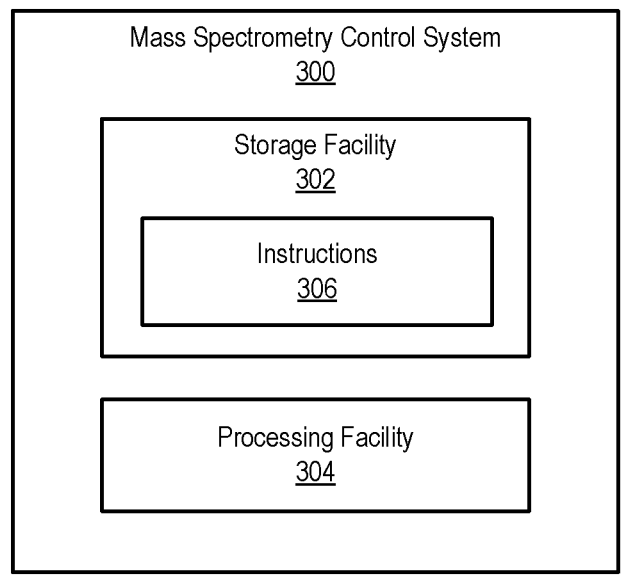
FIG. 3 shows an illustrative mass spectrometry control system.

One or more operations associated with improved methods of targeted multiplexed mass spectrometry may be performed by LC-MS/MS/MS system 100 and/or a mass spectrometry control system. FIG. 3 shows an illustrative mass spectrometry control system 300 ("system 300"). System 300 may be implemented entirely or in part by LC-MS/MS/MS system 100 (e.g., by controller 106 and/or controller 210), such as by an on-board computing system. Alternatively, system 300 may be implemented separately from LC-MS/MS/MS system 100, such as by a personal computing device communicatively coupled to LC-MS/MS/MS system 100.

System 300 may include, without limitation, a storage facility 302 and a processing facility 304 selectively and communicatively coupled to one another. Facilities 302 and 304 may each include or be implemented by hardware and/or software components (e.g., processors, memories, communication interfaces, instructions stored in memory for execution by the processors, etc.). In some examples, facilities 302 and 304 may be distributed between multiple devices and/or multiple locations as may serve a particular implementation.

Storage facility 302 may maintain (e.g., store) executable data used by processing facility 304 to perform any of the operations described herein. For example, storage facility 302 may store instructions 306 that may be executed by processing facility 304 to perform any of the operations described herein. Instructions 306 may be implemented by any suitable application, software, code, and/or other executable data instance.

Storage facility 302 may also maintain any data acquired, received, generated, managed, used, and/or transmitted by processing facility 304. For example, storage facility 302 may maintain LC-MS/MS/MS data (e.g., acquisition list data, parameter data, acquired chromatogram data, and/or mass spectra data).

Processing facility 304 may be configured to perform (e.g., execute instructions 306 stored in storage facility 302 to perform) various processing operations described herein. It will be recognized that the operations and examples described herein are merely illustrative of the many different types of operations that may be performed by processing facility 304. In the description herein, any references to operations performed by system 300 may be understood to be performed by processing facility 304 of system 300. Furthermore, in the description herein, any operations performed by system 300 may be understood to include system 300 directing or instructing another system or device to perform the operations.

Figure 4:
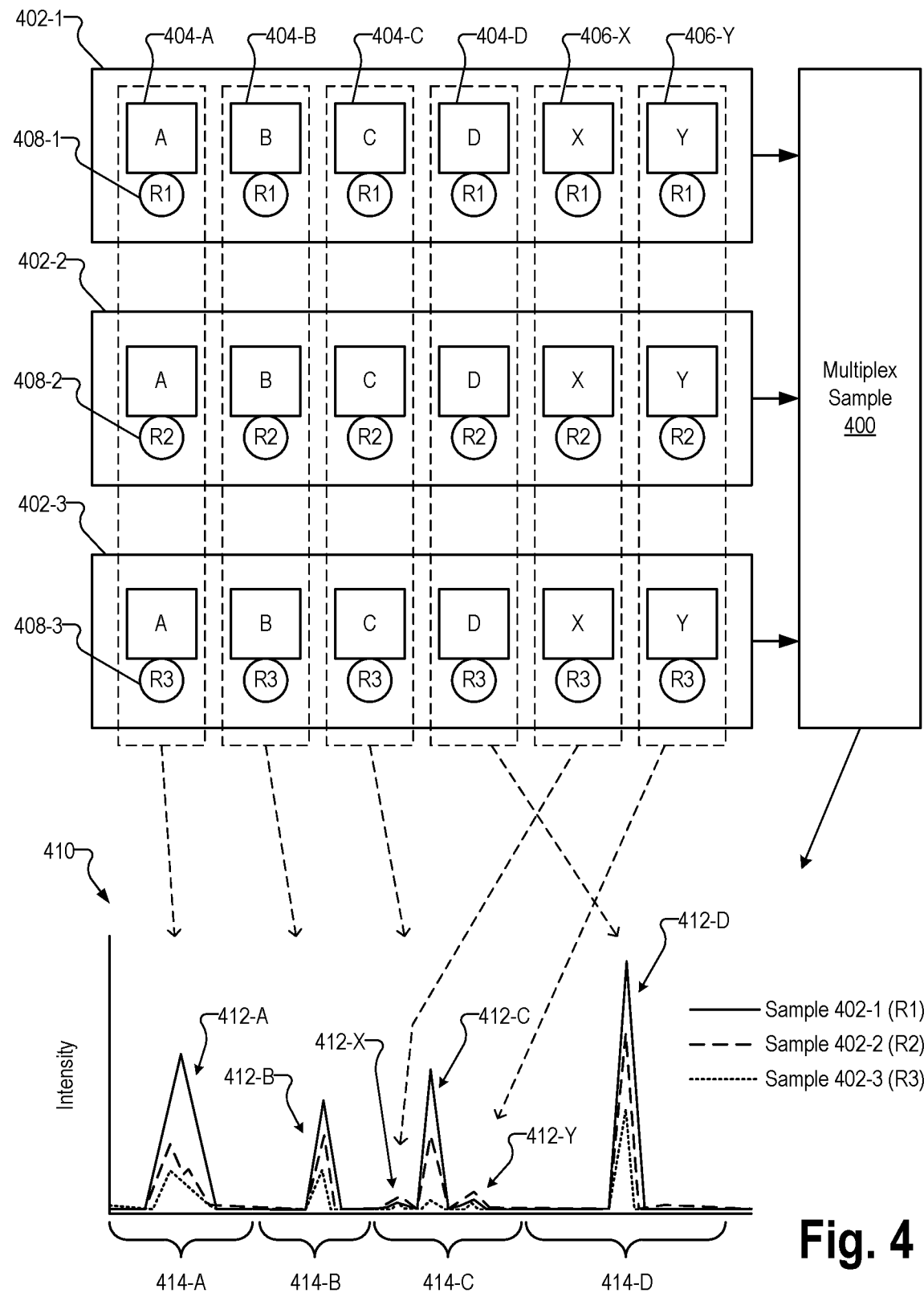
FIG. 4 shows an illustrative multiplex sample that may be analyzed by the LC-MS/MS/MS system of FIG. 1 and/or the mass spectrometry control system of FIG. 3 in a targeted multiplex mass spectrometry experiment.

FIG. 4 shows an illustrative multiplex sample 400 that may be analyzed by LC-MS/MS/MS system 100 and system 300 in a targeted multiplex mass spectrometry experiment. Multiplex sample 400 comprises a plurality of individual samples 402 (e.g., samples 402-1 to 402-3) combined into a single sample (e.g., sample 108) to be injected into LC-MS/MS/MS system 100. Each individual sample 402 includes a plurality of target analytes 404 (e.g., target analytes 404-A to 404-D). In a targeted proteomics experiment, target analytes 404 may be peptides. Samples 402 may also include other components that are not targeted for analysis. For example, FIG. 4 shows that samples 402 include background analytes 406-X and 406-Y. While FIG. 4 shows three samples 402, four target analytes 404, and two background analytes 406, multiplex sample 400 may be formed from any other number of samples 402 (limited only by the number of m/z channels available, e.g., the number of distinct versions of an isobaric tag) and may have any number of target analytes 404 and background analytes 406.

A targeted mass spectrometry experiment may be used to determine a relative quantity of a particular target analyte 404 across each of samples 402. For example, a targeted mass spectrometry experiment may determine a quantity of target analyte 404-A in each of samples 402-2 and 402-3 relative to the quantity of target analyte 404-A in sample 402-1. To this end, each sample 402 is labeled with an isobaric tag 408. Isobaric tags 408 are compounds that react with and attach to target analytes 404. An isobaric tag 408 includes two regions: a reporter region and a balance region. Different versions of an isobaric tag all have the same total mass of reporter region plus balance region, but the reporter region mass and balance region mass vary across different versions of the isobaric tag. As shown in FIG. 4, the components of sample 402-1 (e.g., target analytes 404 and background analytes 406) are labeled with isobaric tag version 408-1, the components of sample 402-2 are labeled with isobaric tag version 408-2, and the components of sample 402-3 are labeled with isobaric tag version 408-3. Reporter ions produced from isobaric tag version 408-1 may have an m/z of 126, reporter ions produced from isobaric tag version 408-2 may have an m/z of 127, and reporter ions produced from isobaric tag version 408-3 may have an m/z of 128. Thus, an isobaric tag-labeled target analyte 404 (e.g., target analyte 404-A) will have the same m/z across all samples 402 so that all versions of isobaric-labeled target analyte 404 will co-elute from column 110. However, when the isobaric tag-labeled target analyte 404 is fragmented by MS2 or MS3, the reporter region falls off and can be targeted for an MS2 or MS3 analysis at each respective reporter ion m/z. The relative intensity of the reporter ions at their respective m/z are indicative of the relative quantities of the target analyte 404 from each sample 402.

Prior to performing a targeted mass spectrometry experiment, a list of analytes that may be included in multiplex sample 400 may be identified as potential targets for a targeted MS3 analysis. The potential target analytes may be selected, for example, based on existing information available, such as a previous discovery experiment or knowledge about the proteins involved in a particular pathway or disease. A characterization analysis of multiplex sample 400 may then be performed to identify which of the potential target analytes are included in multiplex sample 400 and to select the potential analytes that will be subjected to a targeted MS3 analysis. The characterization analysis may determine which of the potential target analytes can actually be observed under a certain set of experimental conditions.

For example, only those potential target analytes that produce abundant (e.g., exceed a threshold intensity level) MS2 fragment ions with isobaric tags may be selected. This may be helpful in targeted proteomics experiments because, when using Trypsin digestion, peptides only have isobaric tags on their N-terminus and on lysine residues, and thus the y-ions of any peptide with arginine at the C terminus will have no isobaric tag. For instance, the potential target analytes may be filtered to include only those potential target analytes that have two or more covarying isobaric-tag labeled MS2 b-ion or y-ion fragments above a threshold MS2 peak area. Any additional or alternative filters may also be used, such as minimum intensity levels, retention time, the presence of interfering analytes, peak shape and separation, and the like. Target analytes that pass through all filters may be selected as target analytes for the targeted analysis to be described below. The size of the list of target analytes may be further constrained by the analysis speed of mass spectrometer 104, since the number of target analytes that mass spectrometer 104 may analyze at any point in time may be limited.

The characterization analysis may also determine the retention times of target analytes, fragment intensities of the target analytes, and target analyte transitions, which information may be used to perform the targeted mass spectrometry experiment.

The characterization analysis may comprise an MS2 analysis performed over a wide precursor range (e.g., 50-1600 m/z, 200-1200 m/z, 400-1000 m/z) in one or more experiments that each cover all or a portion (e.g., 200 m/z) of the full range of possible precursors with a narrow isolation width (e.g., 1 m/z) using a linear ion trap for the product ion collection. As used herein, the term "spectral range" refers to the range of m/z that is measured in a single acquisition, the term "isolation width" refers to a width of the range of precursor ion masses that are isolated for each MS2 acquisition, and the term "precursor range" refers to the total range of m/z of the sampled precursors over multiple acquisitions. An illustrative characterization analysis will now be described.

A multiplex sample containing a plurality of peptide targets may be characterized with MS2 analyses over a precursor range of 400-1000 m/z in three experiments that each cover a 200 m/z portion of the full precursor range with a narrow isolation width (e.g., 1 m/z) using a linear ion trap for the product ion collection. The raw files generated from the MS2 analyses may be analyzed with spectral matching to identify unique target peptides included in the multiplex sample. The unique peptides may be filtered for characteristics that enable high-quality targeted analysis. For example, system 300 may determine metrics (e.g., a cross-correlation value, number of fragments, fragment intensities, correlation value, relative peak area, and summed area) of each peptide and filter the list of identified peptides based on their metrics. A list of the filtered target peptides may be added to an acquisition list for a multiplexed targeted MS3 analysis, which list may include hundreds to a few thousand peptides.

An improved method of multiplexed targeted MS3 analysis includes performing retention time-scheduled targeted MS3 analyses of target analytes included in a multiplex sample and performing periodic MS2 analyses during the targeted MS3 analyses. The targeted MS3 analyses provide reporter ion quantitation with low ratio distortion for relative quantitation of the target analytes. The periodic MS2 analyses provide confirmation of the target analyte identity for the targeted MS3 analyses. The periodic MS2 analyses may also be used for retention time alignment, which allows the retention time-scheduled MS3 acquisition segments to be narrower than otherwise possible, thereby increasing throughput and/or sensitivity. These and other illustrative methods and systems for multiplexed targeted mass spectrometry will be described in more detail below.

The targeted MS3 analyses will now be described with reference to FIG. 4, which shows an illustrative elution profile 410 of multiplex sample 400 (e.g., superimposed XICs of each version of reporter ions 408). As multiplex sample 400 elutes from column 110, target analyte 404-A from samples 402 produces a set of peaks 412-A, target analyte 404-B from samples 402 produces a set of peaks 412-B, and so forth for target analytes 404-C and 404-D and background analytes 406-X and 406-Y. The expected retention time of each target analyte 404 may be known or determined in advance by a characterization analysis, as described above. Accordingly, a targeted MS3 analysis for each target analyte 404 may be scheduled in advance (e.g., by system 300) to be performed during a corresponding acquisition segment 414 (e.g., acquisition segment 414-A for target analyte 404-A, acquisition segment 414-B for target analyte 404-B, acquisition segment 414-C for target analyte 404-C, and acquisition segment 414-D for target analyte 404-D). Each acquisition segment 414 is scheduled based on the expected retention time of the respective target analyte 404 and is performed (e.g., by LC-MS/MS/MS system 100) during the corresponding acquisition segment 414.

An acquisition segment 414 is a period of time surrounding an expected elution peak 412 during which a targeted MS3 analysis is performed. The targeted MS3 analysis targets the reporter ions of the target analyte 404 corresponding to the active acquisition segment 414. For example, in a targeted MS3 analysis first mass analyzer 204-1 isolates first precursor ions of isobaric tag-labeled target analyte 404-A. The first precursor ions are then fragmented in collision cell 206-1 to produce first generation product ions, which are still labeled with isobaric tags 408. The first generation product ions are then further filtered by second mass analyzer 204-2 to produce second precursor ions. The second precursor ions are fragmented in collision cell 206-2 to produce second generation product ions (e.g., reporter ion fragments). Third mass analyzer 204-3 performs a mass analysis of the reporter ion fragments across the range of m/z channels, and the detected signal may be used to generate MS3 mass spectra. In the targeted MS3 analysis, the isolation width of first mass analyzer 204-1 and/or second mass analyzer 204-2 may be set to any suitable value. In some examples, the isolation width is about one (1) m/z.

As shown in elution profile 410, background analytes 406-X and 406-Y co-elute and are co-isolated with target analyte 404-C and thus are analyzed during the targeted MS3 analysis performed during acquisition segment 414-C. Relative quantitation of target analyte 404-C based on the MS3 mass spectra acquired during acquisition segment 414-C would thus be distorted by the presence of mass peaks 412-X and 412-Y produced by background analytes 406-X and 406-Y. Although not shown in FIG. 4, other problems may arise when the expected retention time of a target analyte does not align with the actual retention time. For example, the retention time may shift by up to five minutes in a few weeks. In these scenarios, MS3 mass spectra acquired during an acquisition segment 414 for a target analyte 404 may not represent the target analyte 404.

To address these issues, a plurality of MS2 analyses are performed during each acquisition segment 414. The MS2 mass spectra acquired during acquisition segments 414 may be used during a post-acquisition quantitation process to confirm that MS3 mass peaks representative of the target analyte (and not some other analyte) are present in the MS3 mass spectra acquired during the acquisition segment 414 for the target analyte. When there are multiple sets of MS3 mass peaks in the MS3 mass spectra acquired during the acquisition segment, the MS2 mass spectra may also be used to distinguish MS3 mass peaks representative of background or contaminant analytes (e.g., mass peaks 412-X and 412-Y representative of background analytes 406-X and 406-Y) from the MS3 mass peaks representative of the target analyte (e.g., mass peak 412-C representative of target analyte 404-C). In this way, the relative quantitation may be determined based only on the mass peaks of the target analyte. Post-acquisition methods for determining a relative quantity of a target analyte 404 based on MS2 mass spectra acquired during the acquisition segment 414 for the target analyte 404 and MS3 mass spectra acquired during the acquisition segment 414 for the target analyte 404 will be described below in more detail.

Figure 5:
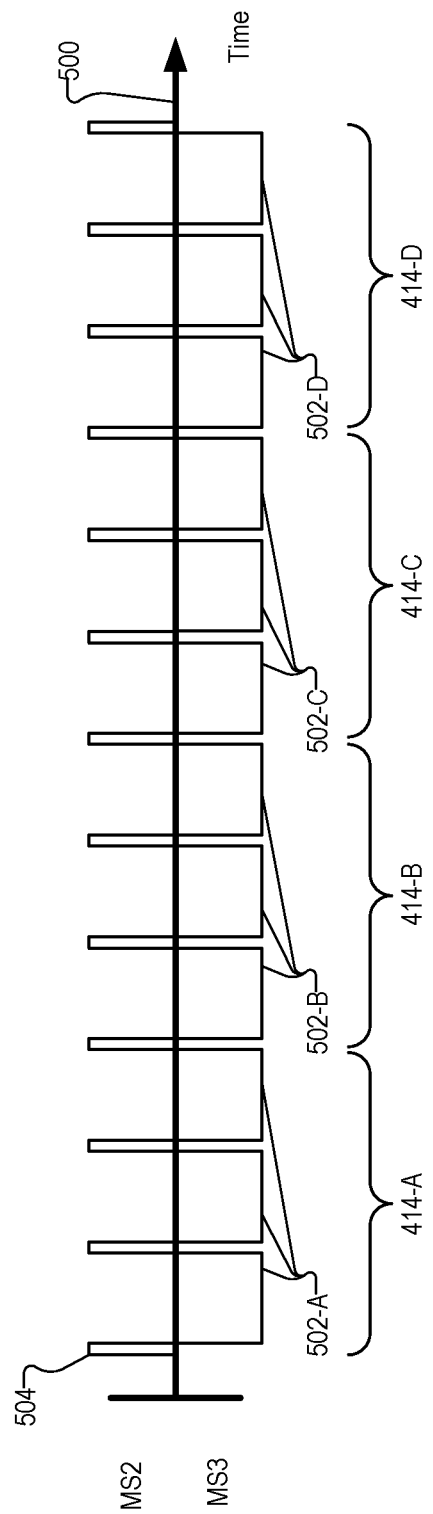
FIG. 5 shows a timeline of an illustrative targeted multiplexed mass spectrometry experiment including targeted MS3 analyses and MS2 analyses.

FIG. 5 shows a timeline 500 of an illustrative targeted multiplexed mass spectrometry experiment including targeted MS3 analyses and MS2 analyses. As shown, a plurality of retention-time scheduled targeted MS3 analyses 502 (e.g., targeted MS3 analyses 502-A, 502-B, 502-C, and 502-D) are performed during acquisition segments 414 (e.g., acquisition segments 414-A to 414-D) as multiplex sample 400 elutes from a column (e.g., column 110). Each targeted MS3 analysis 502 is represented in FIG. 5 by a set of three boxes below timeline 500. A plurality of MS2 analyses 504 (represented by smaller boxes above timeline 500) are also performed during each acquisition segment 414. (For clarity, only one MS2 analysis 504 is labeled in FIG. 5).

Each targeted MS3 analysis 502 and each MS2 analysis 504 includes a plurality of acquisitions (e.g., scans). For example, targeted MS3 analysis 502-A may include N scheduled MS3 acquisitions to be performed during acquisition segment 414-A, where N may range, for example, from a minimum number (e.g., a Nyquist limit, such as 6) to any suitable larger number, such as 10, 20, 100, etc. Thus, each box below timeline 500 may represent a plurality of acquisitions. To illustrate, each MS2 analysis 504 may include 20 MS2 acquisitions with 30 m/z isolation width to cover a 600 m/z precursor range. Targeted MS3 analyses 502 in between consecutive MS2 analyses 504 may contain a plurality of acquisitions for each target. The 20 MS2 acquisitions may take, for example, 200 milliseconds (ms), and the plurality of MS3 acquisitions in between consecutive MS2 analyses 504 may take up to 800 ms, for a 1 second acquisition cycle.

As can be seen in FIG. 5, a targeted MS3 analysis 502 may be temporarily interrupted (e.g., paused) while an MS2 analysis 504 is performed. After completion of an MS2 analysis 504, the targeted MS3 analysis 502 may be resumed if it has not yet finished. For example, targeted MS3 analysis 502-A performed during acquisition segment 414-A may include a set of N scheduled MS3 acquisitions. When an MS2 analysis 504 is performed after having acquired only K total MS3 acquisitions where K<N (e.g., after the first of the three boxes of MS3 analysis 502-A is completed), the targeted MS3 analysis 502-A is resumed at the Kth+1 MS3 acquisition after completion of the MS2 analysis (e.g., the second of the three boxes of MS3 analysis 502-A). In some examples, system 300 may record in a temporary memory (e.g., in a temporary cache or buffer) data identifying the Kth MS3 acquisition when an MS2 analysis 502 is performed. After the MS2 analysis 502 is completed, system 300 may refer to the temporary memory to resume the targeted MS3 analysis 502 beginning at the Kth+1 MS3 acquisition.

As explained above, each targeted MS3 analysis 502 targets a particular target analyte 404 included in the eluting multiplex sample 400 and is performed during an acquisition segment 414 that is scheduled based on an expected retention time of the particular target analyte 404. The acquisition segment 414 may cover a duration of time (e.g., 30 seconds, 1 minute, 90 seconds, 3 minutes, etc.) surrounding the expected retention time of the particular target analyte 404. The retention time scheduling may be performed in any suitable manner. The shorter each acquisition segment 414 is, the more target analytes 404 that can be analyzed and quantitated in the experiment.

While FIG. 5 shows four targeted MS3 analyses 502, the multiplexed targeted mass spectrometry experiment in practice will likely include a larger number of targeted MS3 analyses 502. For example, multiplex sample 400 may include hundreds or thousands of target analytes 404, and thus a corresponding number of targeted MS3 analyses 502 may be performed. Moreover, while FIG. 5 shows that acquisition segments 414 have the same time duration, in other examples the duration of acquisition segments 414 may vary according to the expected peak duration. In further examples, some targeted MS3 analyses 502 may not follow directly after MS2 analyses but may be separated in time by periods during which no targeted MS3 analysis 502 or MS2 analysis 504 is performed. In other examples, some targeted MS3 analyses may be performed one after the other without interruption by an MS2 analysis. Furthermore, while FIG. 5 shows that acquisition segments 414 are each targeted for a single target analyte and do not overlap, in practice there may be multiple acquisition segments 414 that overlap, whether partially or completely, so that many target analytes may be analyzed simultaneously. The mass spectrometer scan rate, the LC peak width, and the desired sampling rate across the LC peak width may determine the maximum number of simultaneously active target analytes that may be scheduled for targeted MS3 analysis.

In some examples, the MS2 analyses 504 take the form of quick MS2 data-independent acquisition (DIA) cycles across a relatively wide precursor range to acquire MS2 mass spectra of product ions derived from target analytes 404 included in multiplex sample 400 as multiplex sample 400 elutes from the column. In the MS2 DIA analyses 504, ions produced from the eluting components are isolated (e.g., in mass analyzer 204-1) with a relatively wide isolation width, fragmented (e.g., in collision cell 206-1), and mass analyzed (e.g., in mass analyzer 204-2) with a wide spectral range.

For data independent acquisition (DIA), an isolation width of a fixed m/z may be sequentially positioned across a wide precursor range to isolate precursor ions for fragmentation. Isolation and fragmentation of one or more precursor ion species is thus not dependent on data acquired in a mass analysis (e.g., a survey scan). In contrast, for data dependent acquisition (DDA), data acquired in one mass analysis is used to select, based on predetermined criteria, one or more ion species or an m/z range for isolation and fragmentation. The spectral range for DIA is usually wider than for DDA.

The MS2 DIA analyses 504 may have any suitable spectral range, precursor range, and isolation width. In some examples, the lower limit of the spectral range of the MS2 analyses 504 is between about 50-400 m/z and the upper limit of the spectral range is between about 1000-1600 m/z. For instance, the spectral range may be 50-1600 m/z, 100-1600 m/z, 200-1400 m/z, 200-1200 m/z, 200-1000 m/z, 400-1600 m/z, 400-1200 m/z, or 400-1000 m/z. In yet further examples, the spectral range may be set based on the m/z range of MS2 fragments derived from the target analytes 404 to be analyzed by the targeted MS3 analyses 502.

In some examples, the isolation width is between about 10-20 m/z. By using a relatively wide isolation width, the full MS2 precursor range can be covered in a relatively short amount of time. For example, an MS2 DIA precursor range of 400-1000 m/z may be covered by 30 MS2 DIA cycles with a 20 m/z isolation width or 60 MS2 DIA cycles with a 10 m/z isolation width. Thus, each MS2 DIA analysis 504 takes only a few seconds (or less) to perform, so that a plurality of MS2 DIA analyses 504 can be performed during a single acquisition segment 414, which may have a duration of up to several minutes.

In other examples, MS2 analyses 504 may take the form of targeted MS2 analyses. In these examples, the targeted MS2 analyses 504 are not limited to DIA analyses that cover an entire precursor m/z range of interest (e.g., 200-1600 m/z), as explained above. Instead, the targeted MS2 analyses 504 may be targeted to analyze only the ions derived from the target analytes that are currently eluting or expected to elute from column 110. For example, the targeted MS2 analyses 504 may be scheduled based on the expected retention time of target analytes as the target analytes elute. Alternatively, the precursor range and/or isolation width for regularly scheduled MS2 analyses 504 may be targeted for the particular ions produced from the target analytes expected to elute during each MS2 analysis 504.

In some examples, any combination of MS2 DIA analyses and targeted MS2 analyses may be performed. For example, targeted MS2 analyses may be performed during acquisition segments 414 for use in quantitating the target analytes, and wide precursor range MS2 DIA analyses may be performed between acquisition segments 414 and/or at regular intervals for use in quantitation of target analytes and/or retention time alignment.

MS2 analyses 504 may be performed with any suitable frequency. For example, MS2 analyses 504 may be performed regularly once every second, once every 2 seconds, once every 3 seconds, once every 5 seconds, or any other suitable frequency. In other examples, MS2 analyses 504 may be performed at non-regular intervals. For instance, MS2 analyses 504 may be performed randomly or performed so that a minimum number of MS2 analyses 504 (e.g., the Nyquist limit, ten, twenty, etc.) are performed during each acquisition segment 414, regardless of duration of the acquisition segment 414. In yet further examples, MS2 analyses 504 may be scheduled based on the expected retention time of the target analytes 404. For example, at least a minimum number of MS2 analyses 504 may be scheduled for each acquisition segment 414. If an acquisition segment 414 is long enough (e.g., exceeds a minimum threshold duration of time), additional MS2 analyses 504 (e.g., more than the minimum) may be scheduled for the acquisition segment 414. In some examples, the interval between MS2 analyses 504 is limited by an MS2 maximum frequency threshold so that a sufficient a number of targeted MS3 scans may be acquired.

System 300 may use the MS2 mass spectra and MS3 mass spectra acquired during an acquisition segment 414 for relative quantitation of the target analyte 404 targeted during the acquisition segment 414. Generally, system 300 may use the MS2 mass spectra as a form of quality control of the MS3 mass spectra. For example, system 300 may use the MS2 mass spectra to confirm that a set of MS3 mass speaks in the MS3 mass spectra acquired during a particular acquisition segment 414 correspond to the target analyte 404 targeted during the acquisition segment 414. If system 300 confirms that a set of MS3 mass peaks corresponds to the target analyte 404, system 300 may quantitate the target analyte 404 based on the set of MS3 mass peaks. On the other hand, if system 300 determines that the MS3 mass spectra does not include a set of MS3 mass peaks that corresponds to the target analyte 404, system 300 may abstain from quantitating the target analyte 404.

System 300 may confirm that a set of MS3 mass peaks acquired during an acquisition segment 414 corresponds to the target analyte 404 targeted in the acquisition segment 414 in any suitable way. In some examples, system 300 may identify an MS3 mass peak in the MS3 mass spectra acquired during an acquisition segment 414 based on a similarity of the MS2 mass spectra acquired during the acquisition segment to library mass spectra for the target analyte 404. The similarity may be determined in any suitable way, such as by a similarity score, which quantifies a degree of similarity between the MS2 mass spectra with library MS2 mass spectra (e.g., MS2 mass spectra acquired during the characterization analysis) for the target analyte 404. The similarity score may be calculated based on any suitable similarity measure or similarity function, such as a cosine similarity. If system 300 determines that the similarity score at any point in time during the acquisition segment exceeds a threshold value (e.g., 0.9 on a similarity scale of 0 to 1), system 300 may confirm that MS3 mass peaks corresponding in time to the highest similarity score represent the target analyte 404.

Figure 6A:
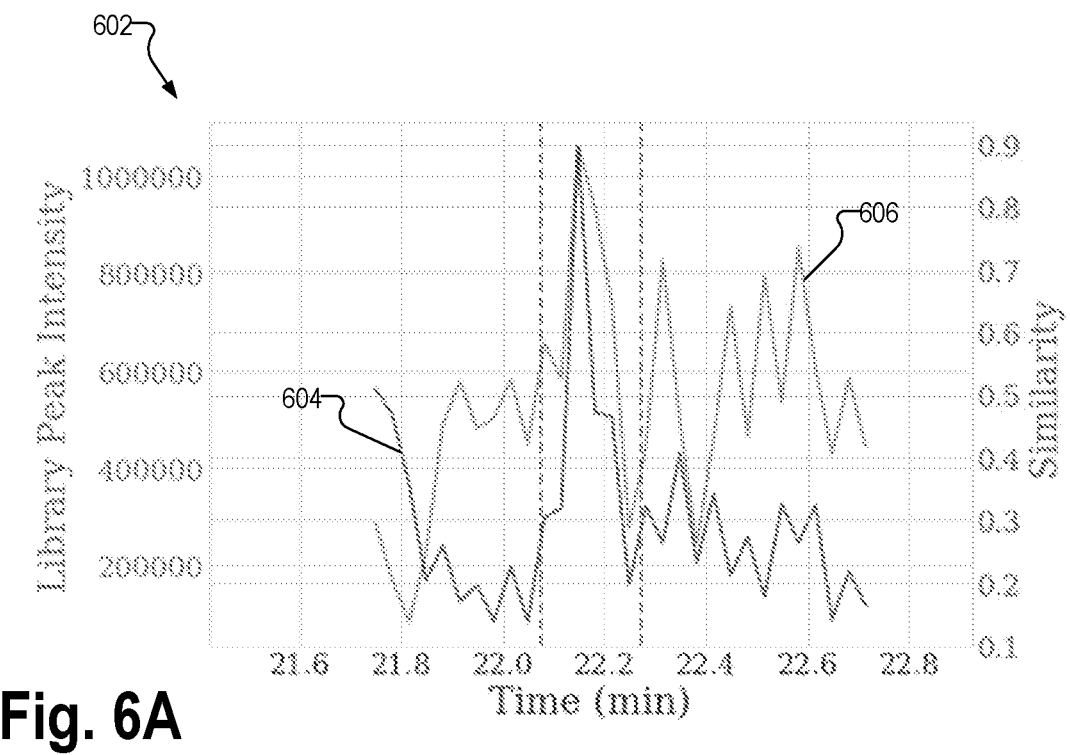
FIGS. 6A and 6B show an illustrative similarity graph over an acquisition segment for a target peptide and an illustrative mass chromatogram for the target peptide over the acquisition segment, which may be used to confirm that MS3 mass peaks acquired during an acquisition segment for a particular target peptide correspond to the particular target peptide.
Figure 6B:
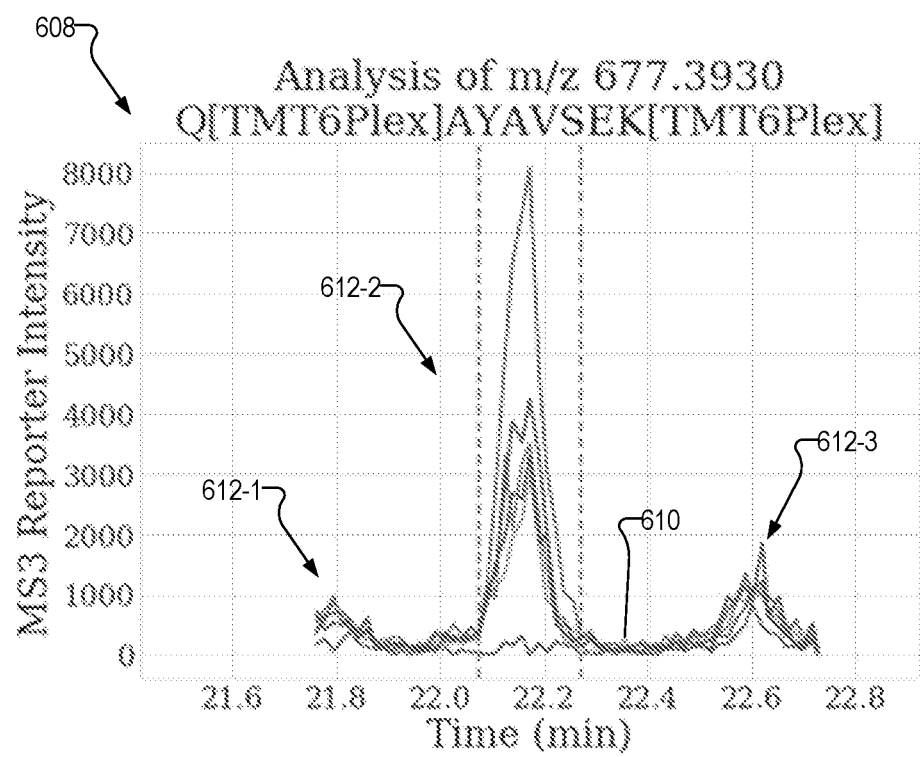

FIGS. 6A and 6B show an illustrative implementation of using the similarity score of the MS2 mass peaks to confirm that MS3 mass peaks acquired during an acquisition segment for a particular target peptide having an m/z of 677.3930 correspond to the particular target peptide. FIG. 6A shows an illustrative similarity graph 602 over an acquisition segment for the target peptide. The acquisition segment begins at about time 21.75 minutes and concludes at about time 22.75 minutes. Similarity graph 602 includes a library curve 604 that plots MS2 library intensity as a function of retention time and a similarity curve 606 that plots the similarity score as a function of retention time. Library curve 604 may be acquired, for example, from a characterization analysis performed prior to the targeted analysis. Similarity curve 606 may be generated by a cosine similarity function based on (e.g., as the dot product of) library curve 604 and MS2 mass spectra acquired during the acquisition segment for the target peptide (e.g., a mass chromatogram obtained based on the MS2 mass spectra). A similarity score close to 1.0 indicates a high degree of similarity while a similarity score close to zero represents a low degree of similarity. As can be seen in similarity graph 602, the peak of the similarity curve 606 is approximately 0.9 at about time 22.1 minutes, which also is the time of the peak of library curve 604 for the target peptide.

FIG. 6B shows an illustrative mass chromatogram 608 for the target peptide over the acquisition segment. Mass chromatogram 608 may be generated based on the MS3 mass spectra that may be acquired during the acquisition segment for the target peptide. Mass chromatogram 608 includes a set of six curves 610 that plot intensity of the reporter ion dissociated from the target peptide as a function of time. Each curve 610 represents the intensity of a distinct reporter ion having an m/z ranging from 126 to 131. As shown, curves 610 include a first set of peaks 612-1 at about time 21.8 minutes, a second set of peaks 612-2 at about time 22.1 minutes, and a third set of peaks 612-3 at about time 22.6 minutes. The multiple sets of peaks 612 acquired during this acquisition segment indicate the likely presence of contaminants or background analytes that were co-isolated with the target peptide.

System 300 may determine, based on the maximum value of similarity curve 606 occurring at about time 22.1 minutes (determined as explained above with reference to FIG. 6A), that second set of peaks 612-2 occurring at about the same time (about time 22.1 minutes) is representative of the target peptide for the acquisition segment. Thus, system 300 may determine the relative quantity of the target peptide based on second set of peaks 612-2 (e.g., by determining the MS3 peak area in the MS mass spectra from about time 22.05 minutes to about time 22.25 minutes). Thus, first and third peaks 612-1 and 612-3 may be attributed to contaminants or background analytes and may be disregarded when quantitating the target peptide.

While the method described with reference to FIGS. 6A and 6B distinguishes the set of mass peaks 612-2 representative of the target peptide from the sets of mass peaks 612-1 and 612-3 representative of contaminants or background analytes, the method may also be used to confirm whether any set of mass peaks acquired during the acquisition segment for the target peptide is representative of the target peptide (e.g., whether there has been a retention time shift). If system 300 determines that no set of mass peaks acquired during the acquisition segment for the target peptide is representative of the target peptide, system 300 may abstain from quantitating the target peptide.

Alternatively to confirming the detection of the target analyte based on a similarity score of the MS2 mass spectra, system 300 may identify an MS3 mass peak based on any one or more additional metrics. For example, system 300 may calculate a quality score for each MS3 mass peak acquired during an acquisition segment and confirm the detection of the target analyte based on the quality score.

Figure 7:
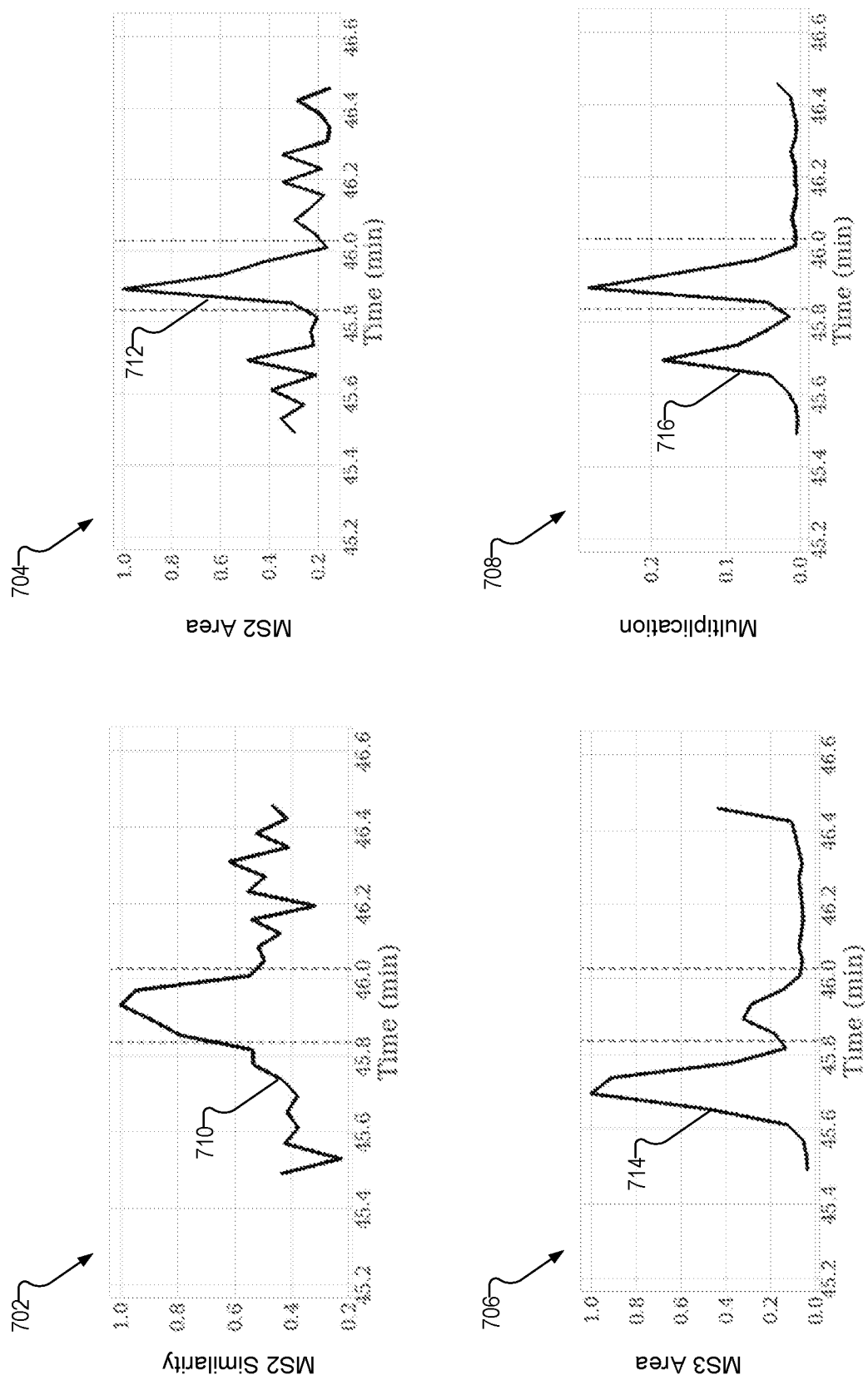
FIG. 7 shows an MS2 similarity graph, an area graph, an MS3 area graph, and a quality score graph that illustrate use of a quality score to confirm the detection of a target peptide acquired during an acquisition segment for the target peptide.

FIG. 7 shows how a quality score may be used to confirm the detection of a target peptide (APLEEIVISNDYLNK) acquired during an acquisition segment for the target peptide. FIG. 7 shows an MS2 similarity graph 702, an MS2 area graph 704, an MS3 area graph 706, and a quality score graph 708. MS2 similarity graph 702 is similar to similarity graph 602 and includes a similarity curve 710 that represents a similarity of the MS2 mass spectra to library mass spectra for the target peptide. MS2 area graph 704 includes an MS2 area curve 712 that plots the relative area of the MS2 mass spectra as a function of retention time, and MS3 area graph 706 includes an MS3 area curve 714 that plots the relative area of the MS3 mass spectra as a function of retention time. Quality score graph 708 includes a quality score curve 716 that plots a quality score as a function of retention time. In this example, the quality score is calculated as the product of similarity curve 710, MS2 area curve 712, and MS3 area curve. As shown in quality score graph 708, the maximum value of the quality score occurs at approximately time 45.9 minutes. It will be recognized that the quality score may be calculated in any other suitable manner using any other suitable metrics and/or combination of metrics.

In the example of FIG. 7, MS2 similarity graph 702 shows that the highest degree of similarity occurs at about time 45.9 minutes. However, as indicated by MS3 area graph 706, this result may not have been readily apparent to a user since the peak on MS3 area curve 714 at time 45.9 minutes is smaller than the peak on MS3 area curve 714 at time 45.7 minutes (which, as the analysis of FIG. 7 shows, is attributable to contaminants or background analytes). However, quality score curve 716 confirms that the smaller MS3 mass peak is representative of the target peptide. Accordingly, system 300 may determine a relative quantity of the target peptide based on the MS3 mass peak occurring at time 45.9 minutes and disregard the MS3 mass peak occurring at time 45.7 minutes.

It will be recognized that in the post-acquisition processing methods described above, confirmation of the target analyte in the MS3 mass spectra may be performed using the MS2 and MS3 mass spectra and related metrics without generating the graphs shown in FIGS. 6A-7.

Various modifications may be made to the systems and methods described herein without departing from the scope and principles of the concepts described herein. For example, system 300 may abstain from quantitating a target analyte if any one or more quantitation conditions are not satisfied, such as when the intensity of the MS2 mass peaks for the target analyte acquired during the acquisition segment are less than a minimum intensity threshold level, or when a measured ratio of the MS2 mass peaks for the target analyte are outside a certain tolerance (e.g., 10%) of the ratio of MS2 mass peaks acquired during a characterization scan.

The systems and methods described above quantitate a target analyte by acquiring multiple targeted MS3 mass spectra across the elution peak for each target analyte and integrating the MS3 mass peak area. This approach enables targeted multiplexed mass spectrometry experiments using lower quality mass analyzers, such as ion traps with less trapping capacity or dynamic range than higher quality mass analyzers such as Orbitrap and ToF mass analyzers. Moreover, acquiring MS3 mass spectra across an acquisition segment increases the reproducibility of the experiment. In further modifications, only one (or any other number less than a Nyquist limit) MS3 mass spectrum is acquired during each targeted MS3 analysis, and system 300 quantitates the target analyte based on the MS3 mass peak intensity of the target analyte rather than on the MS3 mass peak area. This may be possible, for example, when the MS2 analyses are used for retention time alignment and/or when using mass analyzers with higher trapping capacity, such as Orbitrap and ToF mass analyzers. As another example, the target analyte may be quantitated based on the average or weighted average of reportion ion ratios across under-sampled points within a peak boundary given by the MS2 mass spectra, instead of based on just a single peak intensity at the highest point.

In some examples, the MS2 analyses may also be used to detect and correct a retention time shift. For example, system 300 may identify, based on the MS2 DIA mass spectra, an actual retention time of target analytes included in a multiplex sample eluting from a column and adjust one or more acquisition segments (e.g., a start time and/or an end time) to correspond to the actual retention times as determined from the MS2 DIA analyses. Systems and methods for using MS2 DIA analyses to perform a retention time adjustment are described and set forth in U.S. patent application Ser. No. 16/527,990 filed on Jul. 31, 2019.

Figure 8:
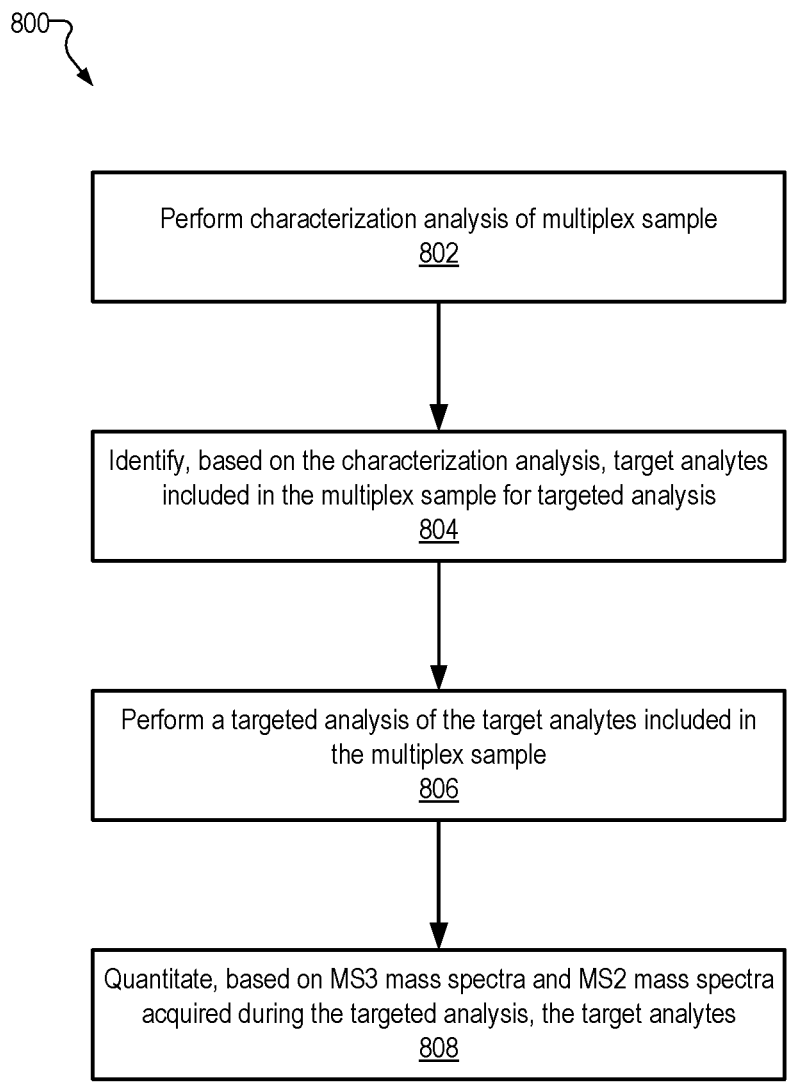
FIG. 8 shows an illustrative method of performing targeted multiplexed mass spectrometry.

FIG. 8 shows an illustrative method 800 of performing targeted multiplexed mass spectrometry. While FIG. 8 shows illustrative operations according to one embodiment, other embodiments may omit, add to, reorder, and/or modify any of the operations shown in FIG. 8. One or more of the operations shown in FIG. 8 may be performed by LC-MS/MS/MS system 100 and/or system 300, any components included therein, and/or any implementations thereof.

In operation 802, a characterization analysis of a multiplex sample is performed. Operation 802 may be performed in any suitable way, including any way described herein.

In operation 804, target analytes included in the multiplex sample are identified, based on the characterization analysis, for targeted analysis. Operation 804 may be performed in any suitable way, including any way described herein.

In operation 806, a targeted analysis of the target analytes included in the multiplex sample is performed. Operation 806 may be performed in any suitable way, including any way described herein.

In operation 808, one or more of the target analytes analyzed by the targeted analysis are quantitated based on MS3 mass spectra and MS2 mass spectra acquired during acquisition segments for the targeted analyses.

Figure 9:
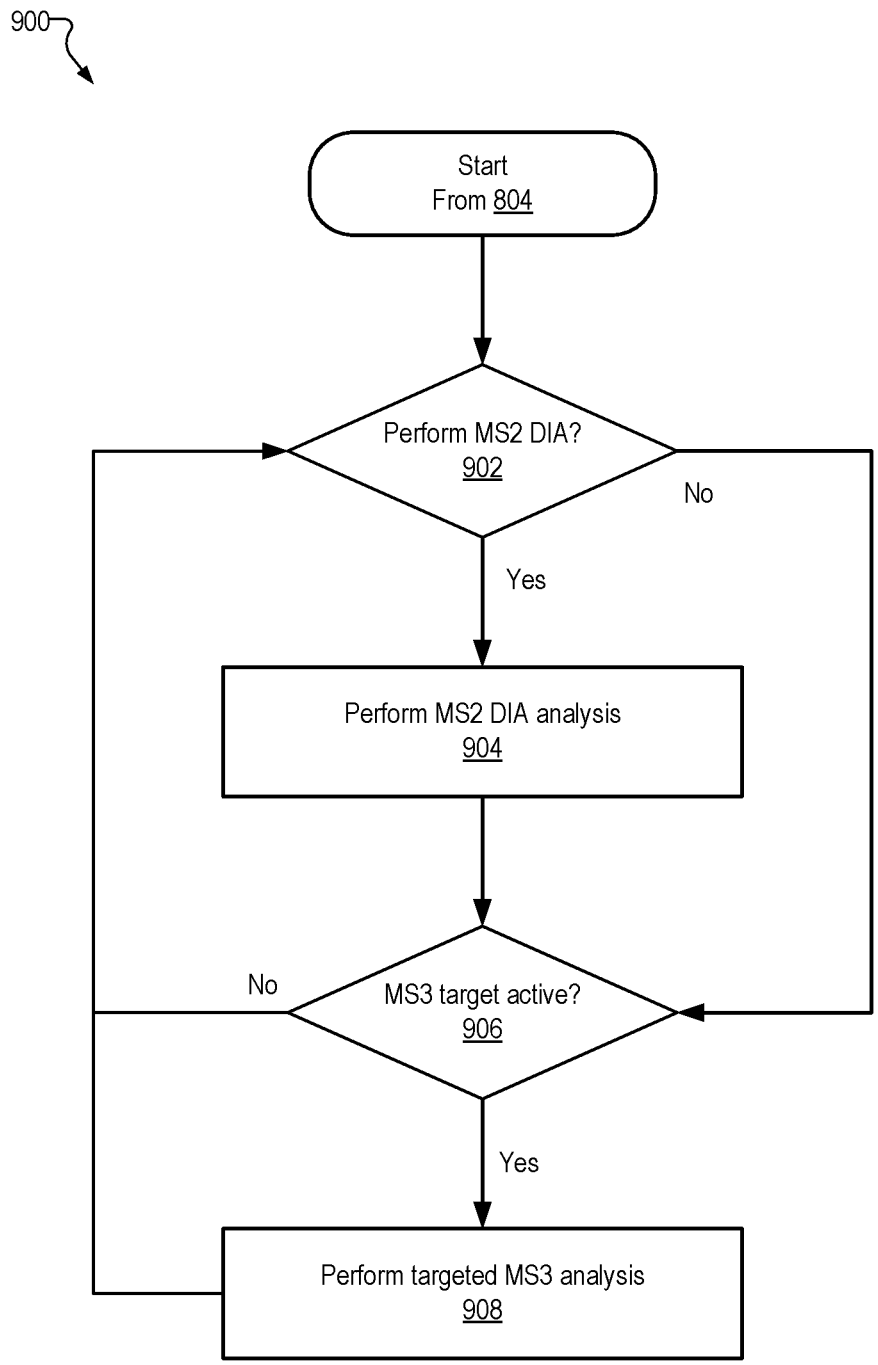
FIG. 9 shows an illustrative method of performing a targeted analysis of target analytes included in a multiplex sample.

FIG. 9 shows an illustrative method 900 of performing operation 806 of method 800. While FIG. 9 shows illustrative operations according to one embodiment, other embodiments may omit, add to, reorder, and/or modify any of the operations shown in FIG. 9. One or more of the operations shown in FIG. 9 may be performed by LC-MS/MS/MS system 100 and/or system 300, any components included therein, and/or any implementations thereof.

In operation 902, system 300 checks whether to perform an MS2 analysis. As mentioned, in some examples MS2 analyses may be performed with a regular frequency. Thus, system 300 may check whether a predetermined amount of time has lapsed since a last MS2 analysis was performed. In other examples, MS2 analyses may be scheduled based on an expected retention time of a target analyte included in the multiplex sample. Accordingly, system 300 may check whether a scheduled acquisition segment is active. If system 300 determines that an MS2 analysis is to be performed, processing proceeds to operation 904. If system 300 determines that an MS2 analysis is not to be performed at the current time, processing proceeds to operation 906.

In operation 904, an MS2 analysis is performed. Operation 904 may be performed in any suitable way, including any way described herein. For example, system 300 may direct LC-MS/MS/MS system 100 to perform an MS2 analysis as described herein. In some examples, operation 904 may be performed during a scheduled acquisition segment for a target analyte.

In operation 906, system 300 checks whether an MS3 targeted analysis is active. Operation 906 may be performed in any suitable way, including any way described herein. For example, system 300 may check whether a current time coincides with a scheduled acquisition segment for a target analyte or whether a scheduled acquisition segment will commence prior to a next MS2 analysis. If system 300 determines that an MS3 targeted analysis is active, processing proceeds to operation 908 to perform a targeted MS3 analysis. If system 300 determines that an MS3 targeted analysis is not active, processing returns to operation 902.

In operation 908, a targeted MS3 analysis is performed during a retention time-scheduled acquisition segment. Operation 908 may be performed in any suitable way, including any way described herein. During the targeted MS3 analysis, processing returns to operation 902 to check whether an MS2 analysis is to be performed. If system 300 determines that an MS2 analysis is to be performed, the targeted MS3 analysis is interrupted or paused (if not yet completed) so that the MS2 analysis may be performed. Upon completion of the MS2 analysis, processing continues to operation 906 and system 300 determines that the MS3 target is active. In operation 908 system 300 resumes the particular targeted MS3 analysis.

Method 900 may continue until terminated, such as by a user or until there are no longer any active MS3 targets (e.g., all acquisition segments have passed).

Figure 10:
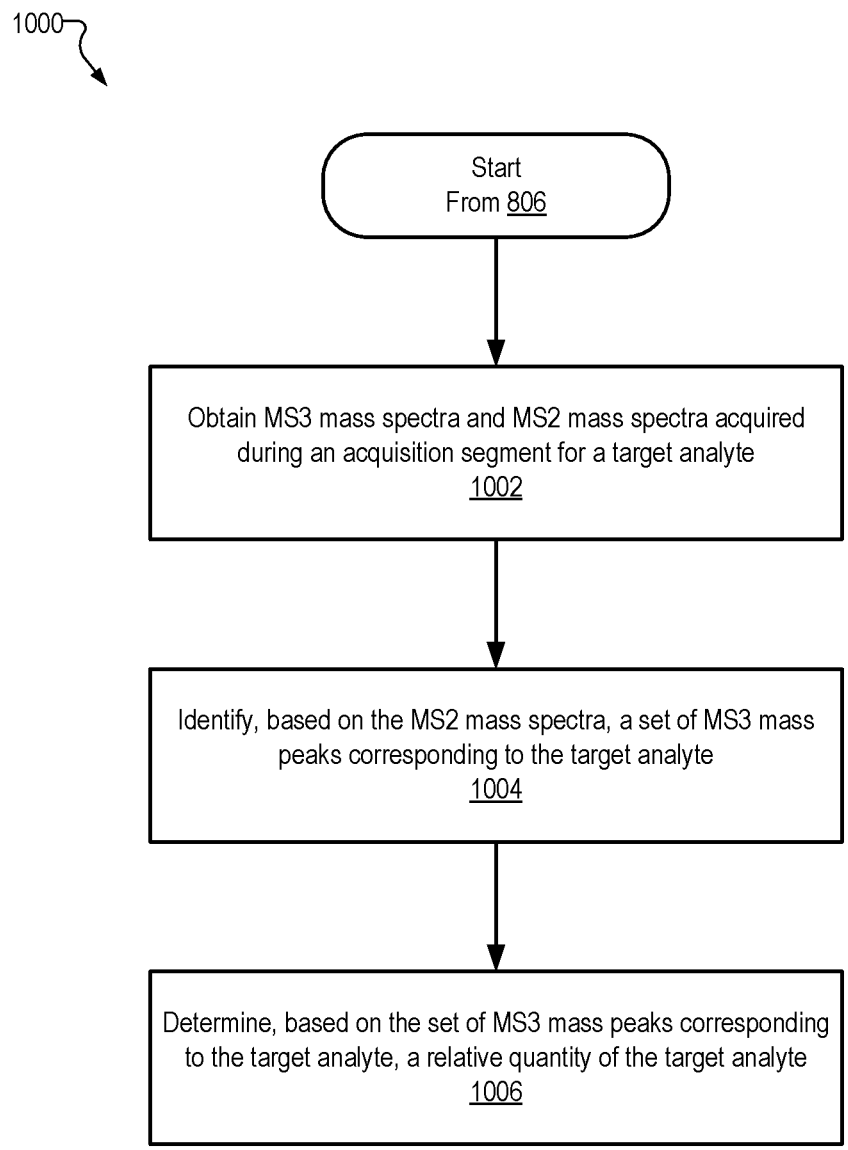
FIG. 10 shows an illustrative method of quantitating, based on MS3 mass spectra and MS2 mass spectra acquired during the targeted analysis of FIG. 9, the target analytes included in the multiplex sample.

FIG. 10 shows an illustrative method 1000 of performing operation 808 of method 800. While FIG. 10 shows illustrative operations according to one embodiment, other embodiments may omit, add to, reorder, and/or modify any of the operations shown in FIG. 10. One or more of the operations shown in FIG. 10 may be performed by LC-MS/MS/MS system 100 and/or system 300, any components included therein, and/or any implementations thereof. Method 1000 may be performed at any suitable time. In some examples, method 1000 is performed after the entire targeted multiplexed mass spectrometry experiment is complete (e.g., after the last acquisition segment has terminated). In other examples, method 1000 may be performed after any one or more acquisition segments terminates.

In operation 1002, system 300 obtains MS3 mass spectra acquired during an acquisition segment for a target and obtains MS2 mass spectra acquired during the acquisition segment. Operation 1002 may be performed in any suitable way, including any way described herein. For example, system 300 may obtain raw data from a mass spectrometer and generate the MS3 mass spectra and/or the MS2 mass spectra. Alternatively, the mass spectrometer may generate and transmit the MS3 mass spectra and/or the MS2 mass spectra to system 300.

In operation 1004, system 300 may identify, based on the MS2 mass spectra, a set of MS3 mass peaks corresponding to the target analyte. Operation 1004 may be performed in any suitable way, including any way described herein. For example, system 300 may identify the set of MS3 mass peaks corresponding to the target analyte based on a similarity score or quality score that is generated based on the MS2 mass spectra. System 300 may identify the set of MS3 mass peaks corresponding to the target analyte as the set of mass peaks corresponding to the similarity score or quality score that satisfies a condition (e.g., corresponds in time to the highest similarity score or quality score, exceeds a minimum threshold value, etc.).

In operation 1006, system may determine, based on the set of MS3 mass peaks corresponding to the target analyte, a relative quantity of the target analyte. Operation 1006 may be performed in any suitable way, including any way described herein.

In certain embodiments, one or more of the systems, components, and/or processes described herein may be implemented and/or performed by one or more appropriately configured computing devices. To this end, one or more of the systems and/or components described above may include or be implemented by any computer hardware and/or computer-implemented instructions (e.g., software) embodied on at least one non-transitory computer-readable medium configured to perform one or more of the processes described herein. In particular, system components may be implemented on one physical computing device or may be implemented on more than one physical computing device. Accordingly, system components may include any number of computing devices, and may employ any of a number of computer operating systems.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a compact disc read-only memory ("CD-ROM"), a digital video disc ("DVD"), any other optical medium, random access memory ("RAM"), programmable read-only memory ("PROM"), electrically erasable programmable read-only memory ("EPROM"), FLASH-EEPROM, any other memory chip or cartridge, or any other tangible medium from which a computer can read.

Figure 11:
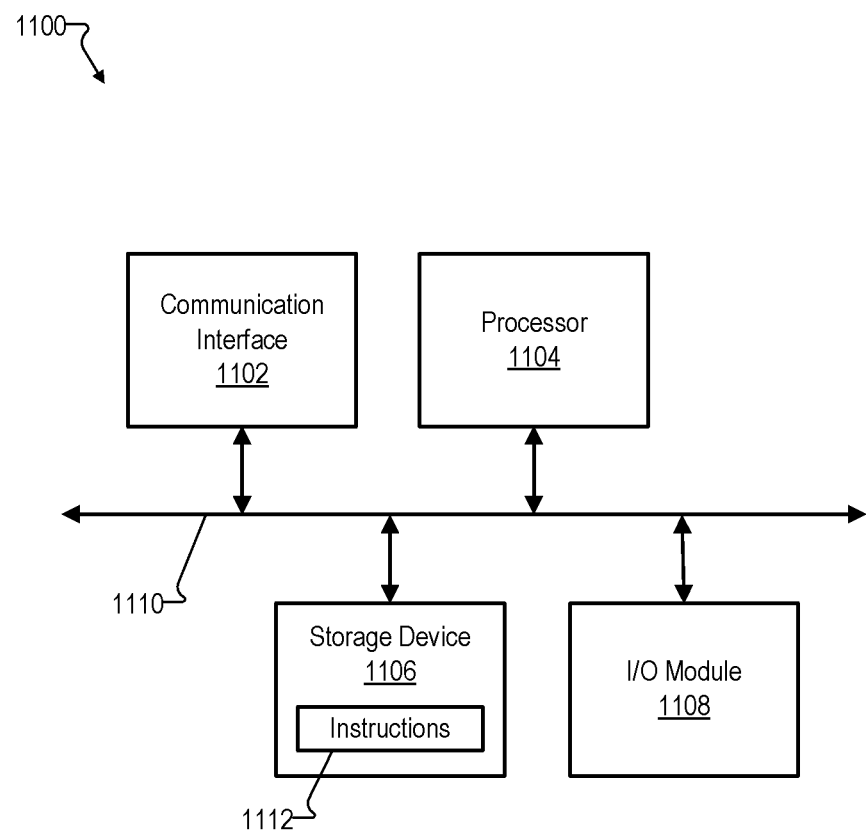
FIG. 11 shows an illustrative computing device.

FIG. 11 shows an illustrative computing device 1100 that may be specifically configured to perform one or more of the processes described herein. As shown in FIG. 11, computing device 1100 may include a communication interface 1102, a processor 1104, a storage device 1106, and an input/output ("I/O") module 1108 communicatively connected one to another via a communication infrastructure 1110. While an illustrative computing device 1100 is shown in FIG. 11, the components illustrated in FIG. 11 are not intended to be limiting. Additional or alternative components may be used in other embodiments. Components of computing device 1100 shown in FIG. 11 will now be described in additional detail.

Communication interface 1102 may be configured to communicate with one or more computing devices. Examples of communication interface 1102 include, without limitation, a wired network interface (such as a network interface card), a wireless network interface (such as a wireless network interface card), a modem, an audio/video connection, and any other suitable interface.

Processor 1104 generally represents any type or form of processing unit capable of processing data and/or interpreting, executing, and/or directing execution of one or more of the instructions, processes, and/or operations described herein. Processor 1104 may perform operations by executing computer-executable instructions 1112 (e.g., an application, software, code, and/or other executable data instance) stored in storage device 1106.

Storage device 1106 may include one or more data storage media, devices, or configurations and may employ any type, form, and combination of data storage media and/or device. For example, storage device 1106 may include, but is not limited to, any combination of the non-volatile media and/or volatile media described herein. Electronic data, including data described herein, may be temporarily and/or permanently stored in storage device 1106. For example, data representative of computer-executable instructions 1112 configured to direct processor 1104 to perform any of the operations described herein may be stored within storage device 1106. In some examples, data may be arranged in one or more databases residing within storage device 1106.

I/O module 1108 may include one or more I/O modules configured to receive user input and provide user output. One or more I/O modules may be used to receive input for a single virtual experience. I/O module 1108 may include any hardware, firmware, software, or combination thereof supportive of input and output capabilities. For example, I/O module 1108 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1108 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1108 is configured to provide graphical data to a display for presentation to a user. The graphical data may be representative of one or more graphical user interfaces and/or any other graphical content as may serve a particular implementation.

In some examples, any of the systems, computing devices, and/or other components described herein may be implemented by computing device 1100. For example, storage facility 302 may be implemented by storage device 1106, and processing facility 304 may be implemented by processor 1104.

It will be recognized by those of ordinary skill in the art that while, in the preceding description, various illustrative embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method of performing targeted mass spectrometry, comprising:
    performing, at a mass spectrometer, a targeted MS3 analysis of an isobaric tag-labeled target analyte included in a multiplex sample eluting from a column, wherein the targeted MS3 analysis is performed during an acquisition segment scheduled based on an expected retention time of the isobaric tag-labeled target analyte;
    performing, during the acquisition segment, a plurality of MS2 analyses of product ions derived from components included in the multiplex sample and eluting from the column; and
    determining, based on MS3 mass spectra acquired by the targeted MS3 analysis and MS2 mass spectra acquired by the plurality of MS2 analyses, a relative quantity of the isobaric tag-labeled target analyte in the multiplex sample.

2. The method of claim 1, wherein the determining the relative quantity of the isobaric tag-labeled target analyte comprises identifying, based on the MS2 mass spectra, MS3 mass peaks included in the MS3 mass spectra and representative of the isobaric tag-labeled target analyte.

3. The method of claim 2, wherein the identifying the MS3 mass peaks representative of the isobaric tag-labeled target analyte comprises spectral matching of the MS2 mass spectra with library MS2 mass spectra for the isobaric tag-labeled target analyte.

4. The method of claim 2, wherein the identifying the MS3 mass peaks representative of the isobaric tag-labeled target analyte comprises:
    determining, based at least in part on the MS2 mass spectra, a quality score of mass peaks included in the MS3 mass spectra; and
    identifying the MS3 mass peaks representative of the isobaric tag-labeled target analyte based on the quality score of the MS3 mass peaks included in the MS3 mass spectra.

5. The method of claim 1, wherein an isolation width of the MS2 analyses is between about 10 m/z and about 20 m/z.

6. The method of claim 1, wherein a spectral range of the MS2 analyses ranges from about 200 m/z to about 1600 m/z.

7. The method of claim 1, wherein a precursor range of the MS2 analyses ranges from about 400 m/z to about 1000 m/z.

8. The method of claim 1, wherein each MS2 analysis is targeted for ions produced from target analytes expected to elute from the column during the MS2 analysis.

9. The method of claim 1, wherein the MS2 analyses are performed with a frequency between about once every second and about once every three seconds.

10. The method of claim 1, wherein the MS2 analyses are scheduled based on the scheduled acquisition segment.

11. The method of claim 1, wherein the mass spectrometer comprises a linear ion trap mass analyzer.

12. A method of performing multiplexed targeted mass spectrometry, comprising:
    acquiring, at a mass spectrometer by a plurality of targeted MS3 analyses during a plurality of acquisition segments, MS3 mass spectra of reporter ions dissociated from a plurality of isobaric tag-labeled target analytes included in a multiplex sample eluting from a column, wherein:
        the multiplex sample comprises a combination of a plurality of individual samples each including one or more of the isobaric tag-labeled target analytes,
        the one or more target analytes included in each individual sample are labeled with a distinct version of an isobaric tag comprising a reporter region from which the reporter ions are derived, and
        each targeted MS3 analysis is performed during an acquisition segment scheduled based on an expected retention time of a target analyte included in the plurality of target analytes;
    periodically acquiring, at the mass spectrometer by a plurality of MS2 analyses performed during the plurality of acquisition segments, MS2 mass spectra of product ions derived from the plurality of target analytes; and determining, by a computing device, a relative quantity of a target analyte included in the plurality of target analytes across the plurality of individual samples based on MS2 mass spectra acquired during an acquisition segment for the target analyte and MS3 mass spectra acquired during the acquisition segment for the target analyte.

13. The method of claim 12, wherein each targeted MS3 analysis comprises acquisition of a plurality of MS3 mass spectra.

14. The method of claim 12, wherein the determining the relative quantity of the target analyte comprises identifying, based on the MS2 mass spectra acquired during the acquisition segment for the target analyte, MS3 mass peaks representative of the target analyte, the MS3 mass peaks representative of the target analyte comprising mass peaks in the MS3 mass spectra acquired during the acquisition segment for the target analyte.

15. The method of claim 14, wherein the identifying the MS3 mass peaks representative of the target analyte is based on spectral matching of the MS2 mass spectra acquired during the acquisition segment for the target analyte with library MS2 mass spectra for the target analyte.

16. The method of claim 14, further comprising:
determining a quality score for each MS3 mass peak acquired during the acquisition segment for the target analyte;
wherein the identifying the MS3 mass peaks representative of the target analyte is based on the quality score for each MS3 mass peak acquired during the acquisition segment for the target analyte.

17. The method of claim 16, wherein the quality score is based on one or more of an MS2 similarity score for each MS2 mass peak, an MS2 mass peak area, and an MS3 mass peak area.

18. The method of claim 12, wherein an isolation width of the MS2 analyses is between about 10 m/z and about 20 m/z.

19. The method of claim 12, wherein a spectral range of the MS2 analyses ranges from about 200 m/z to about 1600 m/z.

20. The method of claim 12, wherein a precursor range of the MS2 analyses ranges from about 400 m/z to about 1000 m/z.

21. The method of claim 12, wherein each MS2 analysis is targeted for ions produced from target analytes expected to elute from the column during the MS2 analysis.

22. The method of claim 12, wherein the MS2 analyses are performed with a frequency between about once per every second and about once every three seconds.

23. The method of claim 12, wherein the MS2 analyses are scheduled based on the scheduled acquisition segments.

24. The method of claim 12, further comprising:
adjusting an acquisition segment of a target analyte based on the MS2 mass spectra.

25. The method of claim 12, wherein the mass spectrometer comprises a linear ion trap mass analyzer.

26. The method of claim 12, further comprising:
supplying a multiplex sample to the column;
directing the plurality of target analytes included in the multiplex sample and eluting from the column to the mass spectrometer; and
producing ions from the plurality of target analytes;
wherein the product ions and the reporter ions are derived from the ions produced from the plurality of target analytes.

27. A system for performing multiplexed targeted mass spectrometry, comprising:
a mass spectrometer configured to receive components included in a multiplex sample and eluting from a chromatography column and mass analyze ions produced from the components, wherein:
the components included in the multiplex sample include a plurality of target analytes;
the multiplex sample comprises a combination of a plurality of individual samples each including one or more of the target analytes; and
the one or more target analytes included in each individual sample are labeled with a distinct version of an isobaric tag comprising a reporter region; and
a computing device configured to:
acquire, by a plurality of targeted MS3 analyses during a plurality of acquisition segments, MS3 mass spectra of reporter ions dissociated from the plurality of target analytes included in the multiplex sample, wherein:
each reporter ion is derived from the reporter region of an isobaric tag; and
each targeted MS3 analysis is performed during an acquisition segment scheduled based on an expected retention time of a target analyte included in the plurality of target analytes;
periodically acquire, by a plurality of MS2 analyses performed during the plurality of acquisition segments, MS2 mass spectra of product ions derived from the plurality of target analytes; and
determine a relative quantity of a target analyte included in the plurality of target analytes across the plurality of individual samples based on MS2 mass spectra acquired during an acquisition segment for the target analyte and MS3 mass spectra acquired during the acquisition segment for the target analyte.

28. The system of claim 27, wherein each targeted MS3 analysis comprises acquisition of a plurality of MS3 mass spectra.

29. The system of claim 27, wherein the determining the relative quantity of the target analyte comprises identifying, based on the MS2 mass spectra acquired during the acquisition segment for the target analyte, MS3 mass peaks representative of the target analyte, the MS3 mass peaks representative of the target analyte comprising mass peaks in the MS3 mass spectra acquired during the acquisition segment for the target analyte.

30. The system of claim 29, wherein the identifying the MS3 mass peaks representative of the target analyte is based on spectral matching of the MS2 mass spectra acquired during the acquisition segment for the target analyte with library MS2 mass spectra for the target analyte.

31. The system of claim 29, wherein the computing device is further configured to:
determine a quality score for each MS3 mass peak acquired during the acquisition segment for the target analyte;
wherein the identifying the MS3 mass peaks representative of the target analyte is based on the quality score for each MS3 mass peak acquired during the acquisition segment for the target analyte.

32. The system of claim 31, wherein the quality score is based on one or more of an MS2 similarity score for each MS2 mass peak, an MS2 mass peak area, and an MS3 mass peak area.

33. The system of claim 27, wherein an isolation width of the MS2 analyses is between about 10 m/z and about 20 m/z.

34. The system of claim 27, wherein a spectral range of the MS2 analyses ranges from about 200 m/z to about 1600 m/z.

35. The system of claim 27, wherein a precursor range of the MS2 analyses ranges from about 400 m/z to about 1000 m/z.

36. The system of claim 27, wherein each MS2 analysis is targeted for ions produced from target analytes expected to elute from the column during the MS2 analysis.

37. The system of claim 27, wherein the MS2 analyses are performed with a frequency between about once per every second and about once every three seconds.

38. The system of claim 27, wherein the MS2 analyses are scheduled based on the scheduled acquisition segments.

39. The system of claim 27, wherein the computing device is further configured to:
 adjust an acquisition segment of a target analyte based on the MS2 mass spectra.

40. The system of claim 27, wherein the mass spectrometer comprises a linear ion trap mass analyzer.

\* \* \* \* \*